United States Patent
Morgan et al.

(10) Patent No.: US 11,964,967 B2
(45) Date of Patent: Apr. 23, 2024

(54) CARDIAC SARCOMERE INHIBITORS

(71) Applicant: Cytokinetics, Inc., South San Francisco, CA (US)

(72) Inventors: Bradley P. Morgan, Oakland, CA (US); Chihyuan Chuang, Millbrae, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 610 days.

(21) Appl. No.: 17/255,336

(22) PCT Filed: Jun. 25, 2019

(86) PCT No.: PCT/US2019/038907
§ 371 (c)(1),
(2) Date: Dec. 22, 2020

(87) PCT Pub. No.: WO2020/005887
PCT Pub. Date: Jan. 2, 2020

(65) Prior Publication Data
US 2021/0253563 A1 Aug. 19, 2021

Related U.S. Application Data

(60) Provisional application No. 62/690,248, filed on Jun. 26, 2018.

(51) Int. Cl.
| C07D 413/12 | (2006.01) |
| A61P 9/04 | (2006.01) |
| C07D 413/04 | (2006.01) |
| C07D 498/10 | (2006.01) |

(52) U.S. Cl.
CPC ............. *C07D 413/12* (2013.01); *A61P 9/04* (2018.01); *C07D 413/04* (2013.01); *C07D 498/10* (2013.01)

(58) Field of Classification Search
CPC ... C07D 413/12; C07D 413/04; C07D 498/10
See application file for complete search history.

(56) References Cited

U.S. PATENT DOCUMENTS

| 5,846,514 A | 12/1998 | Foster |
| 5,919,785 A | 7/1999 | Dinsmore |
| 6,334,997 B1 | 1/2002 | Foster |
| 8,592,426 B2 | 11/2013 | Aebi et al. |
| 9,181,200 B2 | 11/2015 | Oslob |
| 9,199,945 B2 | 12/2015 | Oslob |
| 9,663,516 B2 | 5/2017 | Oslob |
| 9,925,177 B2 | 3/2018 | Oslob |
| 10,836,755 B2* | 11/2020 | Chuang ............... C07D 271/06 |
| 11,414,424 B2 | 8/2022 | Chuang et al. |
| 11,472,796 B2 | 10/2022 | Chuang et al. |
| 2005/0014749 A1 | 1/2005 | Chen et al. |
| 2006/0173183 A1 | 8/2006 | Powers |
| 2006/0241110 A1 | 10/2006 | Morgan |
| 2007/0078126 A1 | 4/2007 | Morgan et al. |
| 2009/0192168 A1 | 7/2009 | Muci et al. |
| 2011/0275673 A1 | 11/2011 | Xiang et al. |
| 2013/0018055 A1 | 1/2013 | Aebi et al. |
| 2013/0296335 A1 | 11/2013 | Morgan et al. |
| 2016/0176868 A1 | 6/2016 | Oslob et al. |
| 2016/0289211 A1 | 10/2016 | Ashcraft |
| 2019/0256504 A1 | 8/2019 | Chuang |
| 2019/0276435 A1 | 9/2019 | Shepard et al. |
| 2020/0000822 A1 | 1/2020 | Kruse et al. |
| 2020/0048235 A1* | 2/2020 | Zhang .................. C07D 413/12 |
| 2020/0054636 A1 | 2/2020 | Semigran et al. |
| 2020/0109148 A1 | 4/2020 | Chuang |
| 2021/0147399 A1 | 5/2021 | Chuang et al. |
| 2021/0276991 A1 | 9/2021 | Morgan et al. |

(Continued)

FOREIGN PATENT DOCUMENTS

| WO | 2003059265 A2 | 7/2003 |
| WO | 2003059265 A3 | 6/2004 |

(Continued)

OTHER PUBLICATIONS

Berge, S.M. et al. (Jan. 1977). "Pharmaceuticals Salts," J. Pharmaceutical Sciences 66:1-19.

(Continued)

*Primary Examiner* — Matthew P Coughlin
(74) *Attorney, Agent, or Firm* — MORRISON & FOERSTER LLP

(57) ABSTRACT

Provided are compounds of Formula (I):

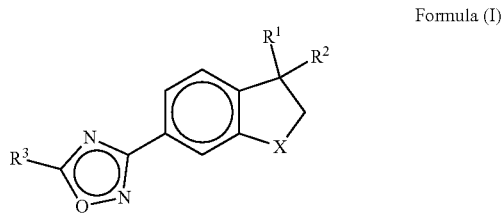

Formula (I)

or a pharmaceutically acceptable salt thereof, wherein X, $R^1$, $R^2$, and $R^3$ are as defined herein. Also provided is a pharmaceutically acceptable composition comprising a compound of Formula (I), or a pharmaceutically acceptable salt thereof. Also provided are methods of using a compound of Formula (I), or a pharmaceutically acceptable salt thereof.

18 Claims, No Drawings

(56) References Cited

U.S. PATENT DOCUMENTS

| | | |
|---|---|---|
| 2021/0323913 A1 | 10/2021 | Martin et al. |
| 2022/0265612 A1 | 8/2022 | Qiao |
| 2022/0274969 A1 | 9/2022 | Tom et al. |
| 2022/0306642 A1 | 9/2022 | Morgan et al. |
| 2022/0315571 A1 | 10/2022 | Tom et al. |
| 2023/0058927 A1 | 2/2023 | Malik et al. |
| 2023/0119665 A1 | 4/2023 | Chuang et al. |
| 2023/0338378 A1 | 10/2023 | Perera et al. |

FOREIGN PATENT DOCUMENTS

| | | | |
|---|---|---|---|
| WO | 2004064730 A2 | 8/2004 | |
| WO | 2004064760 A2 | 8/2004 | |
| WO | 2006009726 A2 | 1/2006 | |
| WO | 2006116150 A1 | 11/2006 | |
| WO | 2007078815 A2 | 7/2007 | |
| WO | 2007117180 A1 | 10/2007 | |
| WO | 2008130320 A2 | 10/2008 | |
| WO | 2008130320 A3 | 12/2008 | |
| WO | 2010033701 A2 | 3/2010 | |
| WO | 2010130796 A1 | 11/2010 | |
| WO | 2012101011 A2 | 8/2012 | |
| WO | 2013048928 A1 | 4/2013 | |
| WO | 2013108227 A1 | 7/2013 | |
| WO | 2014205223 A1 | 12/2014 | |
| WO | 2014205234 A1 | 12/2014 | |
| WO | 2015089337 A1 | 6/2015 | |
| WO | 2017055469 A1 | 4/2017 | |
| WO | 2017103219 A1 | 6/2017 | |
| WO | 2017103223 A1 | 6/2017 | |
| WO | 2017222951 A1 | 12/2017 | |
| WO | 2018063955 A1 | 4/2018 | |
| WO | 2018089433 A1 | 5/2018 | |
| WO | 2018117034 A1 | 6/2018 | |
| WO | 2019144041 A1 | 7/2019 | |
| WO | WO-2019144041 A1 * | 7/2019 | ......... A61K 31/4245 |
| WO | 2019182925 A1 | 9/2019 | |
| WO | 2019226213 A2 | 11/2019 | |
| WO | 2019226213 A3 | 1/2020 | |
| WO | 2020005887 A1 | 1/2020 | |
| WO | 2020005888 A1 | 1/2020 | |
| WO | 2020047323 A1 | 3/2020 | |
| WO | 2020047447 A1 | 3/2020 | |
| WO | 2022047004 A1 | 3/2022 | |

OTHER PUBLICATIONS

Caputo, S. et al. (Nov. 28, 2017). "Diversity-Oriented Synthesis of Various Enantiopure Heterocycles by Coupling Organocatalysis with Multicomponent Reactions," European J. of Chem. 2017(45):6619-6628.

CAS (Dec. 5, 2011). "STN Registry Database Entry for CAS RN 1348860-91-2," accessed Feb. 13, 2021, 1 page.

Dahl, L.K. et al. (Jun. 1, 1962). "Effects of Chronic Excess Salt Ingestion Evidence That Genetic Factors Play an Important Role in Susceptibility to Experimental Hypertension," J Exp Med. 115(6):1173-1190.

Database Registry (Jun. 18, 2008). RN-1028938-65-9 Emory MLSC database: "2, 5-Piperazinediones, 4-[(4-chlorophenyl)methyl]-3-(4-methoxyphenyl)-1-(2-phenylethyl)-," Chemical Abstracts Service, 1 page.

Database Registry (Jun. 24, 2008). RN-1030378-92-7 Emory MLSC database: "1-Piperazineacetamide, 3-(2-fluorophenyl)-N-(2-methylcyclohexyl)-4-[(4-methylphenyl)methyl]-2,5-dioxo," Chemical Abstracts Service, 1 page.

Database Registry (Nov. 4, 2011). RN-1340679-26-6 ChemDiv, Inc.: "2, 5-Piperazinedione, 1-(-3_methylbutyl)-4-(phenylmethyl)-3-(3-pyridinyl)," Chemical Abstracts Service, 3 pages.

Dean, D.C. (2000). "Recent Advances in the Synthesis and Applications of Radiolabeled Compounds for the Drug Discovery and Development," Curr. Pharm. Des. 6(10): Preface Only, 1 page.

Evans, A.E. (Mar. 1981, e-pub. Jan. 9, 2007). "Synthesis of Radiolabeled Compounds," J Radio Anal. Chem. 64(1-2):9-32.

Fillmore, N et al. (2018). "Uncoupling of Glycolysis from Glucose Oxidation Accompanies the Development of Heart Failure with Preserved Ejection Fraction," Mol. Med. 24(3):1-12.

Geisterfer-Lowrance, A.A.T. et al. (May 3, 1996). "A Mouse Model of Familial Hypertrophic Cardiomyopathy," Science 272(5262):731-734.

Green, E. M. et al. (Feb. 5, 2016). "A Small-Molecule Inhibitor of Sarcomere Contractility Suppresses Hypertrophic Cardiomyopathy in Mice," Science 351(6273):617-621.

Guazzi, M. et al. (Sep. 26, 2017). "Cardiopulmonary Exercise Testing: What Is its Value?," J. Am. Coll. Cardiol. 70(13):1618-1636.

Hargrave, J.D. et al. (Nov. 21, 2010, e-pub. Sep. 8, 2010). "Rhodium-Catalysed Conjugate Addition of Arylboronic Acids to Enantiopure Dehydroamino Acid Derivatives," Org. Biomol. Chem. 8(22):5120-5125.

Hartung, A. et al. (Dec. 11, 2012). "One-Pot Ugi/Aza-Michael Synthesis of Highly Substituted 2,5-Diketopiperazines with Anti-Proliferative Properties," Molecules Online 17(12):14685-14699.

International Preliminary Report on Patentability dated Jan. 7, 2021, for Patent Application No. PCT/US2019/038907, filed Jun. 25, 2019, 7 pages.

International Preliminary Report on Patentability dated Jan. 7, 2021, for Patent Application No. PCT/US2019/038908, filed Jun. 25, 2019, 8 pages.

International Preliminary Report on Patentability dated Jul. 30, 2020, for Patent Application No. PCT/US2019/014344, filed Jan. 18, 2019, 11 pages.

International Search Report and Written Opinion of the International Searching Authority dated Aug. 28, 2019, for PCT Patent Application No. PCT/US2019/038907, filed Jun. 25, 2019, 19 pages.

International Search Report and Written Opinion of the International Searching Authority dated Aug. 28, 2019, for PCT Patent Application No. PCT/US2019/038908, filed Jun. 25, 2019, 14 pages.

International Search Report and Written Opinion of the International Searching Authority dated May 20, 2019, for PCT Patent Application No. PCT/US2019/014344, filed Jan. 18, 2019, 19 pages.

International Search Report and Written Opinion of the International Searching Authority dated Nov. 10, 2020, for PCT Patent Application No. PCT/US2020/042387, filed Jul. 16, 2020, 13 pages.

International Search Report and Written Opinion of the International Searching Authority dated Nov. 5, 2020, for PCT Patent Application No. PCT/US2020/042389, filed Jul. 16, 2020, 13 pages.

International Search Report and Written Opinion of the International Searching Authority dated Nov. 6, 2020, for PCT Patent Application No. PCT/US2020/042390, filed Jul. 16, 2020, 14 pages.

Invitation to Pay Additional Fees dated Mar. 28, 2019, for PCT Patent Application No. PCT/US2019/014344, filed Jan. 18, 2019, 14 pages.

Ito, N. (Jan. 2003). "A Medium-Term Rat Liver Bioassay for Rapid In Vivo Detection of Carcinogenic Potential of Chemicals," Cancer Science 94(1):3-8.

Jackson, P. et al. (Aug. 22, 2018). "Appendage and Scaffold Diverse Fully Functionalized Small-Molecule Probes via a Minimalist Terminal Alkyne-Aliphatic Diazirine Isocyanide," J. Org. Chem. 83(18):11245-11253.

Jiang, J. et al. (Oct. 4, 2013, e-pub. Jul. 14, 2014). "Allele-Specific Silencing of Mutant Myh6 Allele in Mice Suppresses Hypertrophic Cardiomyopathy," Science 342(6154):111-114, 11 pages.

Kabalka, G.W. et al. (1989). "The Synthesis of Radiolabeled Compounds via Organometallic Intermediates," Tetrahedron 45(21):6601-6621.

Kaim, L.E. et al. (2007, e-pub. Jan. 24, 2007). "New Indolizine Template from the Ugi Reaction," Synlett 2(1):227-230.

Kim-Mitsuyama, S. et al. (Oct. 2004). "Additive Beneficial Effects of the Combination of a Calcium Channel Blocker and an Angiotensin Blocker on a Hypertensive Rat-Heart Failure Model," Hypertens Res. 27(10):771-779.

(56) References Cited

OTHER PUBLICATIONS

Lee, M. et al. (May 25, 2016). "Convenient asymmetric synthesis of 1,3,4,6-tetrasubstituted 2,5-diketopiperazines," Arkivoc 2016(4):100-113.

Lee, M. et al. (May 19, 2016). "Stereoselective Nucleophile Substitution of [alpha]-Bromo Tertiary Amides for Asymmetric Synthesis of Highly Substituted 2,5-Diketopiperazines," Bull. Korean Chem. Soc. 37(6):981-984.

Lesma, G. et al. (Jun. 18, 2014). "Asymmetric Ugi 3CR on isatin-derived ketimine: synthesis of chiral 3,3-disubstituted 3-aminooxindole derivatives," Beilstein Journal of Organic Chemistry 10:1383-1389.

Malhotra, R. et al. (Aug. 2016, e-pub. Jun. 8, 2016). "Cardiopulmonary Exercise Testing in Heart Failure," JACC Heart Fail 4(8):607-616.

Mamoun, O. et al. (1995, e-pub. Sep. 23, 2006). "Synthesis of Methyl 3-Amino-3-pyrrolidinecarboxylates: A Convenient Access to Cucurbitine and Analogues," Synthetic Communications 25(9):1295-1302.

Parker, M.F.L. et al. (Jan. 23, 2014). "Acceleration of an Aromatic Claisen Rearrangement via a Designed Spiroligozyme Catalyst that Mimics the Ketosteroid Isomerase Catalytic Dyad," J. American Chem. Soc. 136(10):3817-3827.

Pettersson, M. et al. (Oct. 1, 2015). "Design, Synthesis and Evaluation of 2,5-Diketopiperazines as Inhibitors of the MDM2-p53 Interaction," PLOS ONE 10(10):e0137867, 19 pages.

Philipson, D. J. et al. (2017, e-pub. Aug. 31, 2017). "Emerging Pharmacologic and Structural Therapies for Hypertrophic Cardiomyopathy," Heart Fail Rev. 22(6):879-888.

Pyne, S.G. et al. (1993). "Asymmetric Synthesis of Chiral Cyclic Amino Acids by Diels-Alder Reactions of (2S)- and (2R)-4-Methyleneoxazolidin-5-ones," Aust. J Chem. 46(1):73-93.

Rowin, E.J. et al. (Nov. 2017). "Role of Exercise Testing in Hypertrophic Cardiomyopathy," JACC: Cariovasc Imaging. 10(11):1374-1386.

Sakata, Y. et al. (Jan. 2001). "Renin Angiotensin System-Dependent Hypertrophy as a Contributor to Heart Failure in Hypertensive Rats: Different Characteristics From Renin Angiotensin System-Independent Hypertrophy," J. Am. Coll. Cardiol. 37(1):293-299.

Santra, S. et al. (Apr. 1, 2011, e-pub. Feb. 25, 2011). "A Rapid, One-Pot, Microwave-Influenced Synthesis of Spiro-2,5-diketopiperazines via a Cascade Ugi/6-Exo-Trig Aza-Michael Reaction," Journal of Organic Chemistry 76(7):2261-2264.

Taub, P.R. et al. (Oct. 1, 2013). "Perturbations in Skeletal Muscle Sarcomere Structure in Patients with Heart Failure and Type 2 Diabetes: Restorative Effects of (-)-epicatechin-rich Cocoa," Clinical Science 125(8):383-389.

U.S. Appl. No. 17/013,472, filed Sep. 4, 2020, by Chuang Chihyuan et al.

U.S. Appl. No. 17/255,379, filed Jun. 25, 2019, by Bradley Morgan et al.

Walvoord, R.R. et al. (Nov. 4, 2014). "Quantification of Electrophilic Activation by Hydrogen-Bonding Organocatalysts", J. American Chem. Soc. 136(45):16055-16065.

Williams, R. et al. (Nov. 3, 1992). "Asymmetric synthesis of S-(-)-Cucurbitine," Tetrahedron Letters 33(45):6755-6758.

Williams, R.M. et al. (Nov. 1982). "A New and Efficient Cyclization Reaction to Construct the Bicyclomycin Ring System: Synthesis of N,N'-Dimethyl-4-desmethylenebicyclomycin," Journal of the American Chemical Society 104(22):6092-6099.

Yates, P. et al. (Jan. 1, 1983). "Synthesis of Piperazine-2,5-diones Related to Bicyclomycin: 3-acetoxy-1,4-dibenzyl-3-[1-(2-methoxyethyl)- and 1-(2-hydroxyethyl)ethenyl]piperazine-2,5-dione. 1. Route via Acyclic Intermediates," Canadian Journal of Chemistry 61(3):519-528.

Yoshifuji, S. et al. (Aug. 1995). "Stereospecific Synthesis of (R)- and (S)-Baclofen and (R)- and (S)-PCPGABA [4-Amino-2-(4-chlorophenyl)butyric Acid] via (R)- and (S)-3-(4-Chlorophenyl)pyrrolidines," Chem Pharm Bull 42(8) 1302-1306.

ANONYMOUS (2022). "Empowering Muscle Empowering Lives: Sarcomere Directed Therapies," Cytokinetics, 57 pages.

CAS (Nov. 12, 2007). "STN Registry Database entry for CAS RN 953060-71-4," entry date of Nov. 12, 2007, accessed Jul. 15, 2021, 5 pages.

CAS Registry No. 1384080-08-3. (Jul. 23, 2012). "1,2,4-Oxadiazole-5-carboxylic acid, 3-[4-[(acetylamino)methyl]phenyl]-, methyl ester," 3 pages.

CAS Registry No. 1384080-74-3. (Jul. 23, 2012). "1,2,4-Oxadiazole-5-carboxylic acid, 3-[4-[(acetylamino)methyl]phenyl]-, ethyl ester," 2 Pages.

CAS Registry No. 1826330-24-8 (Dec. 10, 2015). "2-Pyridinamine, 5-Methyl-N-[[4-[3-(Trifluoromethyl)-1H-Pyrazol-1-yl] Phenyl] Methyl]-," 1 page.

CAS Registry No. 1826379-58-1 (Dec. 10, 2015). "2-Pyridinamine, 4-Methyl-N-[[4-[3-(Trifluoromethyl)-1H-Pyrazol-1-yl] Phenyl] Methyl]-," 1 page.

CAS Registry No. 1829209-70-2 (Dec. 14, 2015). "2-Pyridinamine, 3-Methyl-N-[[4-[3-(Trifluoromethyl)-1H-Pyrazol-1-yl] Phenyl] Methyl]-," 1 page.

CAS Registry No. 1829877-40-8. (Dec. 15, 2015). "2-Pyridinamine, 6-Methyl-N-[[4-[3-(Trifluoromethyl)-1H-Pyrazol-1-yl] Phenyl] Methyl]-," 1 page.

CAS Registry No. 2093706-41-1. (Apr. 30, 2017). "2-Pyrazinecarbonitrile, 5-[[[4-[3-(Trifluoromethyl)-1H-Pyrazol-1-yl]Phenyl]Methyl]Amino]-," Enamine LLC, 1 page.

Examination Report dated Aug. 17, 2023, for European U.S. Appl. No. 19/703,917. 5 pages.

International Preliminary Report on Patentability dated Jan. 27, 2022, for Patent Application No. PCT/US2020/042387, filed Jul. 16, 2020, 8 pages.

International Preliminary Report on Patentability dated Jan. 27, 2022, for Patent Application No. PCT/US2020/042389, filed Jul. 16, 2020, 8 pages.

International Preliminary Report on Patentability dated Jan. 27, 2022, for Patent Application No. PCT/US2020/042390, filed Jul. 16, 2020, 8 pages.

International Search Report and Written Opinion of the International Searching Authority dated May 17, 2022, for PCT Patent Application No. PCT/US2022/018725, filed on Mar. 3, 2022, 12 pages.

Martin, R. et al. (2009). "Total Synthesis of Pentabromo- and Pentachloropseudilin, and Synthetic Analogues—Allosteric Inhibitors of Myosin ATPase," Angew Chem Int Ed Engl. 48(43):8042-8046.

U.S. Appl. No. 18/355,195, filed Jul. 19, 2023, for Stephen B. Heitner et al.

U.S. Appl. No. 18/365,038, filed Aug. 3, 2023, for Fady Malik et al.

\* cited by examiner

CARDIAC SARCOMERE INHIBITORS

CROSS REFERENCE TO RELATED APPLICATIONS

This application is a national stage application under 35 U.S.C. § 371 of International Application No. PCT/US2019/038907, filed internationally on Jun. 25, 2019, which claims priority to U.S. Provisional Application No. 62/690,248, filed Jun. 26, 2018, entitled "CARDIAC SARCOMERE INHIBITORS," the contents of which are hereby incorporated by reference in their entirety for all purposes.

FIELD

Provided herein are heterocyclic compounds, pharmaceutical compositions comprising such compounds, and methods of treating various cardiac diseases and conditions with such compounds.

BACKGROUND

The disclosure relates to certain chemical entities that selectively modulate the cardiac sarcomere, and specifically to certain chemical entities, pharmaceutical compositions and methods for treating various cardiac diseases and conditions.

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either 'hyper' or 'hypo' contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic Ca' and cyclic AMP concentrations in the inotropically stimulated myocardium. Given the limitations of current agents, new approaches are needed to improve cardiac function in HCM and HFpEF.

There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac myosin) has been identified as an important means to achieve this improved therapeutic index. The present disclosure provides such agents (particularly cardiac sarcomere inhibitors) and methods for their use. These agents are selective allosteric inhibitors of cardiac myosin that have little to no effect on smooth muscle myosin. Benefits of these compounds include a wider therapeutic index, less impact on cardiac relaxation, better pharmacokinetics, and better safety.

The present disclosure provides chemical entities, pharmaceutical compositions and methods for the treatment of heart failure including HCM and HFpEF. The compositions are inhibitors of the cardiac sarcomere, for example, inhibitors of cardiac myosin.

BRIEF SUMMARY

In one aspect, provided is a compound of Formula (I), or a pharmaceutically acceptable salt thereof:

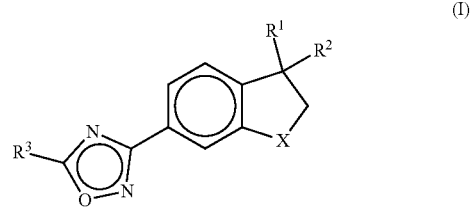

wherein:

X is —O— or —$CH_2$—;

$R^1$ is H and $R^2$ is —C(O)$NHR^a$; or, $R^1$ and $R^2$ taken together are —$CH_2$OC(O)NH—;

$R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and $R^a$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl.

In some embodiments of Formula (I), X is —$CH_2$—. In other embodiments X is —O—.

In some embodiments of Formula (I), $R^1$ is H and $R^2$ is —C(O)$NHR^a$. In some such embodiments, $R^a$ is substituted or unsubstituted alkyl, substituted or unsubstituted aryl, or substituted or unsubstituted heteroaryl. In some embodiments, $R^a$ is substituted or unsubstituted phenyl, substituted or unsubstituted pyrazolyl, or substituted or unsubstituted pyrdinyl. In some embodiments, $R^a$ is selected from the group consisting of:

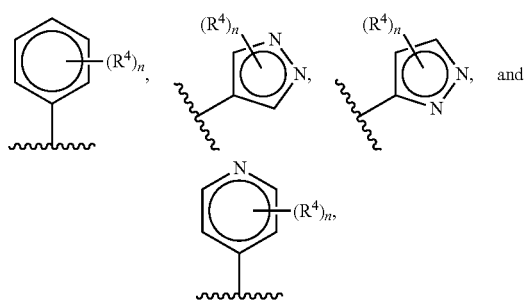

wherein n is 1-3; each $R^4$ is independently selected from the group consisting of alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, and oxo. In one such embodiment, n is 1. In another such embodiment, n is 2. In a further embodiment, n is 3.

In further embodiments of Formula (I), $R^a$ is methyl, ethyl, propyl, or butyl. In other embodiments, $R^a$ is ethyl.

In other embodiments of Formula (I), $R^a$ is selected from the group consisting of:

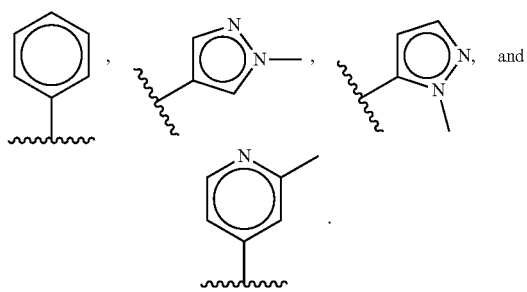

In some embodiments of Formula (I), $R^1$ and $R^2$ taken together are —CH$_2$OC(O)NH—.

In additional embodiments of Formula (I), including the embodiments provided herein wherein $R^1$ is H and $R^2$ is —C(O)NHR$^a$ or wherein $R^1$ and $R^2$ taken together are —CH$_2$OC(O)NH—, $R^3$ is substituted or unsubstituted alkyl, or substituted or unsubstituted cycloalkyl. In some embodiments, $R^3$ is an unsubstituted $C_{1-8}$ alkyl. In some embodiments, $R^3$ is methyl, ethyl, propyl, isopropyl, or butyl. In some embodiments, $R^3$ is an unsubstituted $C_{1-6}$ cycloalkyl. In other embodiments, $R^3$ is cyclopropyl. In another embodiment, $R^3$ is haloalkyl. In further embodiments, $R^3$ is —CHF$_2$.

Provided in some embodiments are compounds selected from the group consisting of compounds of Table 1, or a pharmaceutically acceptable salt thereof.

Provided in some aspects is a pharmaceutical composition containing a compound of Formula (I) or any variation thereof, or a pharmaceutically acceptable salt thereof, and a pharmaceutically acceptable excipient.

Provided in some aspects are methods of treating heart disease in a subject in need thereof, the method comprising administering to the subject a compound of Formula (I) or any variation thereof, or a pharmaceutically acceptable salt thereof, or a pharmaceutical composition containing a compound of Formula (I) or any variation thereof or a pharmaceutically acceptable salt thereof. In some embodiments, the heart disease is hypertrophic cardiomyopathy (HCM). In some embodiments, the HCM is obstructive or nonobstructive or is caused by sarcomeric and/or non-sarcomeric mutations. In some embodiments, the heart disease is heart failure with preserved ejection fraction (HFpEF). In some embodiments, the heart disease is selected from the group consisting of diastolic dysfunction, primary or secondary restrictive cardiomyopathy, myocardial infarction and angina pectoris, and left ventricular outflow tract obstruction. In some embodiments, the heart disease is hypertensive heart disease, congenital heart disease, cardiac ischemia, coronary heart disease, diabetic heart disease, congestive heart failure, right heart failure, cardiorenal syndrome, or infiltrative cardiomyopathy. In some embodiments, the heart disease is a condition that is or is related to cardiac senescence and/or diastolic dysfunction due to aging. In some embodiments, the heart disease is a condition that is or is related to left ventricular hypertrophy and/or concentric left ventricular remodeling.

Provided in other aspects are methods of treating a disease or condition associated with HCM in a subject in need thereof, wherein the method comprises administering to the subject a compound of Formula (I) or any variation thereof, or a pharmaceutically acceptable salt thereof, or a pharmaceutical composition containing a compound of Formula (I) or any variation thereof or a pharmaceutically acceptable salt thereof. In some embodiments, the disease or condition is selected from the group consisting of Fabry's Disease, Danon Disease, mitochondrial cardiomyopathies, and Noonan Syndrome.

Provided in some aspects are methods of treating a disease or condition that is associated with secondary left ventricular wall thickening in a subject in need thereof, wherein the method comprises administering to the subject a compound of Formula (I) or any variation thereof, or a pharmaceutically acceptable salt thereof, or a pharmaceutical composition containing a compound of Formula (I) or any variation thereof or a pharmaceutically acceptable salt thereof. In some embodiments, the disease or condition is selected from the group consisting of hypertension, valvular heart diseases (such as aortic stenosis and Mitral valve regurgitation), metabolic syndromes (such as diabetes and obesity), end stage renal disease, scleroderma, sleep apnea, amyloidosis, Fabry's disease, Friedreich Ataxia, Danon disease, Noonan syndrome, and Pompe disease.

Provided in other aspects are methods of treating a disease or condition that is associated with small left ventricular cavity and cavity obliteration, hyperdynamic left ventricular contraction, myocardial ischemia, or cardiac fibrosis. Also provided are methods of treating muscular dystrophies (e.g., Duchenne muscular dystrophy) or glycogen storage diseases.

Also provided are methods of inhibiting the cardiac sarcomere, wherein the method involves contacting the cardiac sarcomere with a compound of Formula (I) or any variation thereof, or a pharmaceutically acceptable salt thereof, or a pharmaceutical composition containing a compound of Formula (I) or any variation thereof or a pharmaceutically acceptable salt thereof.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (Ia), (Ib), (Ic), (Id), (Ie), and (If), including all substructures, subgenera, preferences, embodiments, examples and particular compounds defined and/or described herein. References to a compound of Formula (I) and subgroups thereof, such as Formula (Ia), (Ib), (Ic), (Id), (Ie), and (If), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (Ia), (Ib), (Ic), (Id), (Ie), and (If), include polymorphs, solvates, co-crystals, isomers, tautomers and/or oxides thereof. In some embodiments, references to a compound of Formula (I) and subgroups thereof, such as Formula (Ia), (Ib), (Ic), (Id), (Ie), and (If), include polymorphs, solvates, and/or co-crystals thereof. In some embodiments, references to a compound of Formula (I) and subgroups thereof, such as Formula (Ia), (Ib), (Ic), (Id), (Ie), and (If), include isomers, tautomers and/or oxides thereof. In some embodiments, references to a compound of Formula (I) and subgroups thereof, such as Formula (Ia), (Ib), (Ic), (Id), (Ie), and (If), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Cycloalkynyl" refers to an unsaturated hydrocarbon group within a cycloalkyl having at least one site of acetylenic unsaturation (i.e., having at least one moiety of the formula CC). Cycloalkynyl can consist of one ring, such as cyclooctyne, or multiple rings. One cycloalkynyl moiety is an unsaturated cyclic hydrocarbon having from 5 to 10 annular carbon atoms (a "$C_5$-$C_{10}$ cycloalkynyl"). Examples include cyclopentyne, cyclohexyne, cycloheptyne, cyclooctyne, cyclononyne, and the like.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluoro, chloro, bromo or iodo.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocyclyl, aralkyl, aminosulfonyl, sulfonylamino, sulfonyl, oxo, and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2$H, $^3$H, $^{11}$C, $^{13}$C and/or $^{14}$C. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to modulate the the cardiac sarcomere. As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of the cardiac sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

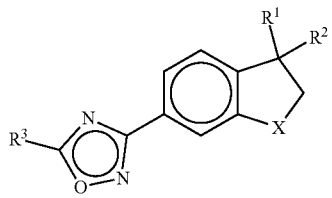

or a pharmaceutically acceptable salt thereof, wherein:
- X is —O— or —CH$_2$—;
- R$^1$ is H and R$^2$ is —C(O)NHR$^a$; or R$^1$ and R$^2$ taken together are —CH$_2$OC(O)NH—;
- R$^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl; and
- R$^a$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl.

In some embodiments of Formula (I), R$^1$ and R$^2$ taken together are —CH$_2$OC(O)NH—. In other embodiments, R$^1$ is H and R$^2$ is —C(O)NHR$^a$.

In some variations of Formula (I), R$^3$ is substituted or unsubstituted alkyl. In some embodiments, R$^3$ is an unsubstituted C$_{1-8}$ alkyl. In some embodiments, R$^3$ is substituted alkyl. In other embodiments, R$^3$ is methy, ethyl, propyl, isopropyl, or butyl. In other embodiments, R$^3$ is methyl, ethyl or isopropyl. In other embodiments, R$^3$ is haloalkyl. In some such embodiments, R$^3$ is —CF$_3$, —CHF$_2$, —CH$_2$F. In other embodiments, R$^3$ is —CH$_2$F. In other embodiments, R$^3$ is substituted or unsubstituted cycloalkyl. In some embodiments, R$^3$ is an unsubstituted C$_{1-6}$ cycloalkyl. In other embodiments, R$^3$ is cyclopropyl, cyclobutyl, cyclopentyl, or cyclohexyl. In some embodiments, R$^3$ is cyclopropyl. In some embodiments, R$^3$ is substituted cycloalkyl.

In some embodiments of Formulas (I), R$^a$ is substituted or unsubstituted alkyl. In some embodiments, R$^a$ is unsubstituted alkyl. In some embodiments, R$^a$ is substituted alkyl. In some embodiments, R$^a$ is methyl, ethyl, propyl, isopropyl, or butyl. In some such embodiments, R$^a$ is ethyl. In yet other embodiments, R$^a$ is substituted or unsubstituted aryl. In other embodiments, R$^a$ is substituted aryl. In further embodiments, R$^a$ is unsubstituted aryl. In some such embodiments, R$^a$ is phenyl. In additional embodiments, R$^a$ is substituted or unsubstituted heteroaryl. In other embodiments, R$^a$ is unsubstituted heteroaryl.

In some embodiments of Formulas (I), R$^a$ is substituted or unsubstituted pyrazolyl, or substituted or unsubstituted pyridinyl. R$^a$ is selected from the group consisting of:

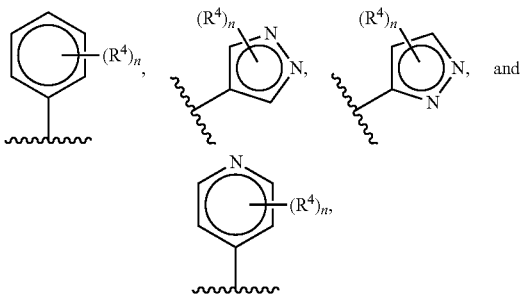

wherein n is 1-3; each R$^4$ is independently selected from the group consisting of alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, and oxo. In one such embodiment, n is 1. In another such embodiment, n is 2. In a further embodiment, n is 3.

In some embodiments of Formula (I), R$^a$ is selected from the group consisting of:

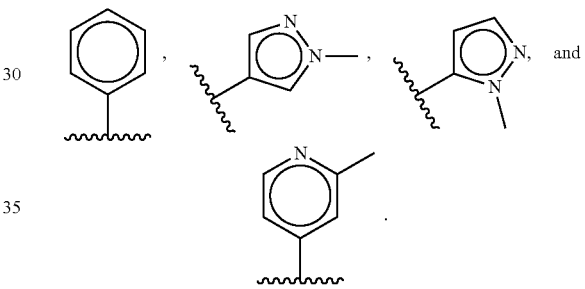

In some embodiments of Formula (I), R$^3$ is an unsubstituted C$_{1-8}$ alkyl. In some embodiments, R$^3$ is substituted alkyl. In other embodiments, R$^3$ is methyl, ethyl, propyl, isopropyl, or butyl. In other embodiments, R$^3$ is methyl, ethyl, or isopropyl. In other embodiments, R$^3$ is unsubstituted alkenyl. In further embodiments, R$^3$ is unsubstituted alkynyl. In other embodiments, R$^3$ is an unsubstituted C$_{1-6}$ cycloalkyl. In other embodiments, R$^3$ is unsubstituted cycloalkenyl. In other embodiments, R$^3$ is unsubstituted cycloalkynyl. In other embodiments, R$^3$ is unsubstituted heterocyclyl. In other embodiments, R$^3$ is unsubstituted aryl. In other embodiments, R$^3$ is unsubstituted heteroaryl.

In some embodiments of Formulas (I), R$^a$ is unsubstituted alkyl. In other embodiments, R$^a$ is unsubstituted alkenyl. In other embodiments, R$^a$ is unsubstituted alkynyl. In other embodiments, R$^a$ is unsubstituted cycloalkyl. In other embodiments, R$^a$ is unsubstituted cycloalkenyl. In other embodiments, R$^a$ is unsubstituted cycloalkynyl. In other embodiments, R$^a$ is unsubstituted heterocyclyl. In other embodiments, R$^a$ is unsubstituted aryl. In yet other embodiments, R$^a$ is unsubstituted heteroaryl.

In some embodiments of Formula (I), R$^3$ is substituted alkyl. In other embodiments, R$^3$ is substituted alkenyl. In further embodiments, R$^3$ is substituted alkynyl. In other embodiments, R$^3$ is substituted cycloalkyl. In other embodiments, R$^3$ is substituted cycloalkenyl. In other embodiments, R$^3$ is substituted cycloalkynyl. In other embodiments, R$^3$ is substituted heterocyclyl. In other embodiments, $R^3$ is substituted aryl. In other embodiments, $R^3$ is substituted heteroaryl.

In some embodiments of Formula (I), $R^a$ is substituted alkyl. In other embodiments, $R^a$ is substituted alkenyl. In other embodiments, $R^a$ is substituted alkynyl. In other embodiments, $R^a$ is substituted cycloalkyl. In other embodiments, $R^a$ is substituted cycloalkenyl. In other embodiments, $R^a$ is substituted cycloalkynyl. In other embodiments, $R^a$ is substituted heterocyclyl. In other embodiments, $R^a$ is substituted aryl. In yet other embodiments, $R^a$ is substituted heteroaryl.

In another aspect, the compound of Formula (I) is a compound of Formula (Ia), (Ib) or (Ic):

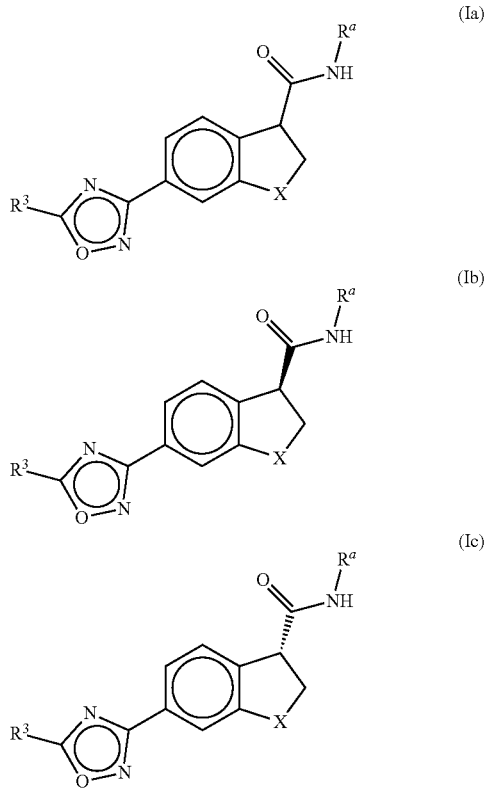

or a pharmaceutically acceptable salt thereof, wherein X, $R^3$, and $R^a$ are as defined for Formula (I) or any variation or embodiment thereof.

In some embodiments of Formula (Ia), (Ib) or (Ic), X is —O—. In other embodiments, X is —CH$_2$—.

In some embodiments of Formula (Ia), (Ib) or (Ic), X is —CH$_2$— and $R^3$ is substituted or unsubstituted alkyl. In some such embodiments, $R^3$ is an unsubstituted $C_{1-8}$ alky. In other embodiments, $R^3$ is substituted alkyl. In other embodiments, $R^3$ is methy, ethyl, propyl, isopropyl, or butyl. In other embodiments, $R^3$ is methyl, ethyl or isopropyl. In other embodiments, $R^3$ is haloalkyl. In some such embodiments, $R^3$ is —CF$_3$, —CHF$_2$, —CH$_2$F. In other embodiments, $R^3$ is —CH$_2$F.

In some embodiments of Formula (Ia), (Ib) or (Ic), X is —CH$_2$— and $R^3$ is substituted or unsubstituted cycloalkyl. In some embodiments, $R^3$ is unsubstituted cycloalkyl. In some embodiments, $R^3$ is substituted cycloalkyl. In other embodiments, $R^3$ is cyclopropyl, cyclobutyl, cyclopentyl, or cyclohexyl. In some embodiments, $R^3$ is cyclopropyl.

In some embodiments of Formula (Ia), (Ib) or (Ic), X is —CH$_2$— and $R^a$ is substituted or unsubstituted alkyl. In other such embodiments, $R^a$ is unsubstituted alkyl. In some embodiments, $R^a$ is substituted alkyl. In some embodiments, $R^a$ is methyl, ethyl, propyl, isopropyl, or butyl. In some such embodiments, $R^a$ is ethyl. In yet other embodiments, $R^a$ is substituted or unsubstituted aryl. In other embodiments, $R^a$ is substituted aryl. In further embodiments, $R^a$ is unsubstituted aryl. In some such embodiments, $R^a$ is phenyl. In additional embodiments, $R^a$ is substituted or unsubstituted heteroaryl. In other embodiments, $R^a$ is unsubstituted heteroaryl.

In some embodiments of Formula (Ia), (Ib) or (Ic), X is —CH$_2$— and $R^a$ is selected from the group consisting of:

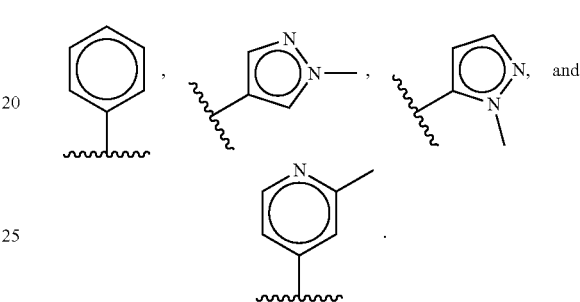

In some such embodiments, $R^3$ is substituted or unsubstituted alkyl, or substituted or unsubstituted cycloalkyl. In some embodiments, $R^3$ is an unsubstituted $C_{1-8}$ alkyl. In some embodiments, $R^3$ is substituted alkyl. In some embodiments, $R^3$ is methyl, ethyl, propyl, isopropyl, or butyl. In other embodiments, $R^3$ is methyl, ethyl, or isopropyl. In other embodiments, $R^3$ is haloalkyl. In some such embodiments, $R^3$ is —CF$_3$, —CHF$_2$, —CH$_2$F. In other embodiments, $R^3$ is —CH$_2$F. In other embodiments, $R^3$ is an unsubstituted $C_{1-6}$ cycloalkyl. In further embodiments, $R^3$ is cyclopropyl, cyclobutyl, cyclopentyl, or cyclohexyl. In additional embodiments, $R^3$ is cyclopropyl.

In some embodiments of Formula (Ia), (Ib), or (Ic), X is —CH$_2$— and $R^3$ is substituted or unsubstituted alkyl and $R^a$ is substituted or unsubstituted alkyl. In some embodiments, $R^3$ and $R^a$ are independently methyl, ethyl, propyl, isopropyl, or butyl. In other embodiments, $R^3$ and $R^a$ are independently ethyl or isopropyl. In further embodiments, $R^3$ and $R^a$ are ethyl. In other embodiments, $R^3$ is haloalkyl. In some such embodiments, $R^3$ is —CF$_3$, —CHF$_2$, —CH$_2$F. In other embodiments, $R^3$ is —CH$_2$F.

In some embodiments of Formula (Ia), (Ib) or (Ic), X is —CH$_2$— and $R^3$ is substituted or unsubstituted alkyl and $R^a$ is substituted or unsubstituted aryl, or substituted or unsubstituted heteroaryl. In some embodiments, $R^3$ is methyl, ethyl, propyl, isopropyl, or butyl, and $R^a$ is substituted or unsubstituted phenyl. In some embodiments, $R^3$ is ethyl and $R^a$ is phenyl. In other such embodiments, $R^3$ is methyl, ethyl, isopropyl, or butyl; and $R^a$ is substituted or unsubstituted heteroaryl. In other embodiments, $R^a$ is substituted or unsubstituted pyrazolyl or pyridinyl. In some embodiments, $R^3$ is methyl, ethyl or isopropyl and $R^a$ is substituted pyrazolyl or pyridinyl. In some such embodiments, $R^3$ is haloalkyl and $R^a$ is substituted or unsubstituted heteroaryl. In some such embodiments, $R^3$ is —CF$_3$, —CHF$_2$, —CH$_2$F, and $R^a$ is substituted pyrazolyl or pyridinyl. In other embodiments, $R^3$ is —CH$_2$F and $R^a$ is substituted pyridinyl.

In some embodiments of Formula (Ia), (Ib), or (Ic), X is —CH₂— and R³ is substituted or unsubstituted cycloalkyl and Rᵃ is substituted or unsubstituted heteroaryl. In some such embodiments, R³ is cyclopropyl, cyclobutyl, cyclopentyl, or cyclohexyl, and Rᵃ is substituted or unsubstituted pyrazolyl or pyridinyl. In other embodiments, R³ is cyclopropyl and Rᵃ is substituted pyridinyl.

In another aspect, the compound of Formula (I) is a compound of Formula (Id), (Ie) or (If):

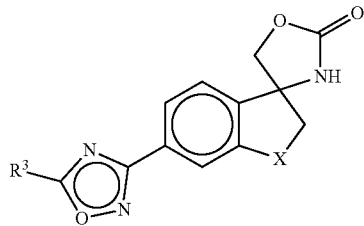
(Id)

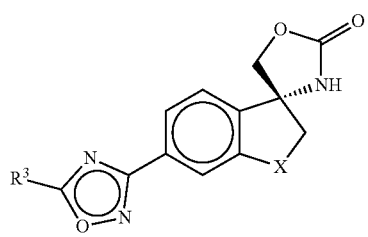
(Ie)

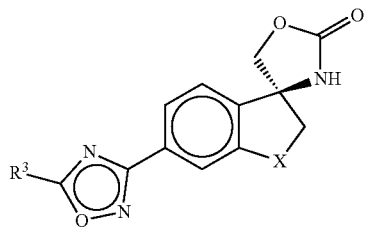
(If)

or a pharmaceutically acceptable salt thereof, wherein X and R³ are as defined for Formula (I) or any variation or embodiment thereof.

In some embodiments of Formula (Id), (Ie) or (If), X is —O—. In other embodiments, X is —CH₂—.

In some embodiments of Formula (Id), (Ie), or (If), X is —CH₂— and R³ is substituted or unsubstituted alkyl, or substituted or unsubstituted cycloalkyl. In some embodiments, R³ is an unsubstituted $C_{1-8}$ alkyl. In some embodiments, R³ is substituted alkyl. In some such embodiments, R³ is methyl, ethyl, propyl, isopropyl, or butyl. In other embodiments, R³ is methy, ethyl, or isopropyl. In some embodiments, R³ is an unsubstituted $C_{1-6}$ cycloalkyl. In further embodiments, R³ is cyclopropyl, cyclobutyl, cyclopentyl, or cyclohexyl. In some embodiments, R³ is cyclopropyl. In other embodiments, R³ is haloalkyl. In some such embodiments, R³ is —CF₃, —CHF₂, —CH₂F. In other embodiments, R³ is —CH₂F.

In some embodiments of Formula (Id), (Ie), or (If), X is —O— and R³ is substituted or unsubstituted alkyl. In some embodiments, R³ is an unsubstituted $C_{1-8}$ alkyl. In some embodiments, R³ is substituted alkyl. In some such embodiments, R³ is methyl, ethyl, propyl, isopropyl, or butyl. In other embodiments, R³ is methy, ethyl, or isopropyl. In further embodiments, R³ is ethyl.

In some embodiments, provided herein are compounds and pharmaceutically acceptable salts thereof described in Table 1.

TABLE 1

| Cmpd No. | Structure | Name |
|---|---|---|
| 1 | 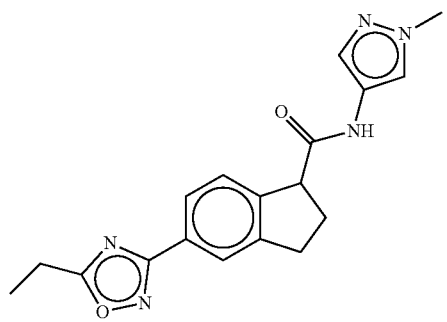 | 5-(5-ethyl-1,2,4-oxadiazol-3-yl)-N-(1-methyl-1H-pyrazol-4-yl)-2,3-dihydro-1H-indene-1-carboxamide |

TABLE 1-continued
| Cmpd No. | Structure | Name |
|---|---|---|
| 2 | 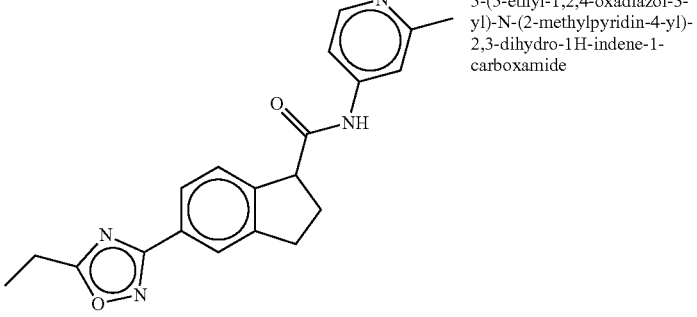 | 5-(5-ethyl-1,2,4-oxadiazol-3-yl)-N-(2-methylpyridin-4-yl)-2,3-dihydro-1H-indene-1-carboxamide |
| 3 | 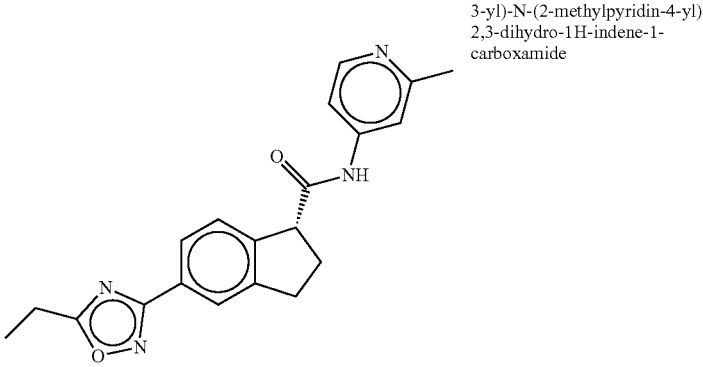 | (R)-5-(5-ethyl-1,2,4-oxadiazol-3-yl)-N-(2-methylpyridin-4-yl)-2,3-dihydro-1H-indene-1-carboxamide |
| 4 | 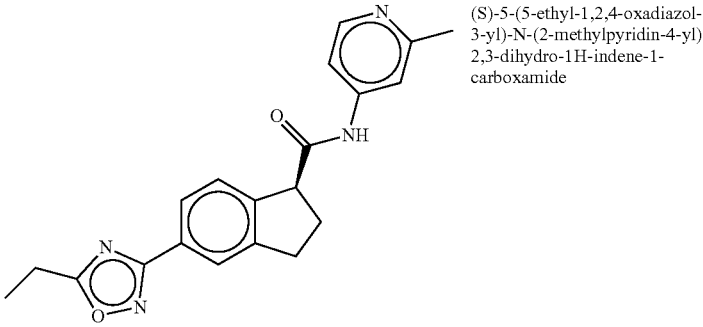 | (S)-5-(5-ethyl-1,2,4-oxadiazol-3-yl)-N-(2-methylpyridin-4-yl)-2,3-dihydro-1H-indene-1-carboxamide |
| 5 | 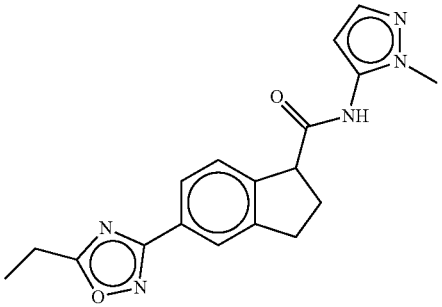 | 5-(5-ethyl-1,2,4-oxadiazol-3-yl)-N-(1-methyl-1H-pyrazol-5-yl)-2,3-dihydro-1H-indene-1-carboxamide |

TABLE 1-continued

| Cmpd No. | Structure | Name |
|---|---|---|
| 6 | 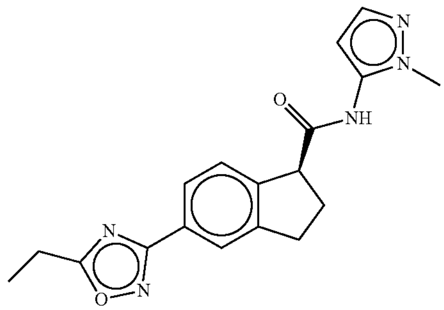 | (S)-5-(5-ethyl-1,2,4-oxadiazol-3-yl)-N-(1-methyl-1H-pyrazol-5-yl)-2,3-dihydro-1H-indene-1-carboxamide |
| 7 | 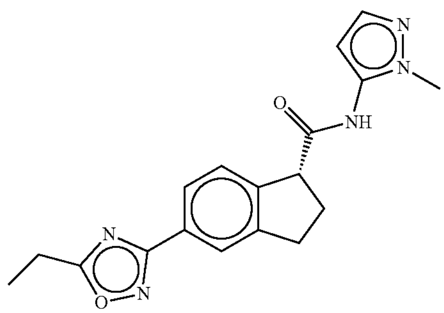 | (R)-5-(5-ethyl-1,2,4-oxadiazol-3-yl)-N-(1-methyl-1H-pyrazol-5-yl)-2,3-dihydro-1H-indene-1-carboxamide |
| 8 | 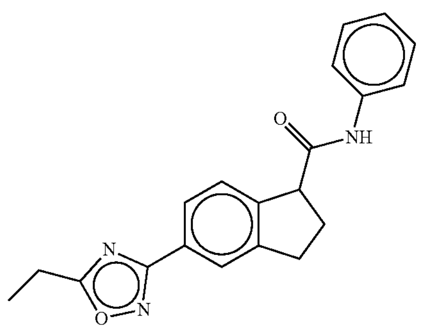 | 5-(5-ethyl-1,2,4-oxadiazol-3-yl)-N-phenyl-2,3-dihydro-1H-indene-1-carboxamide |
| 9 | 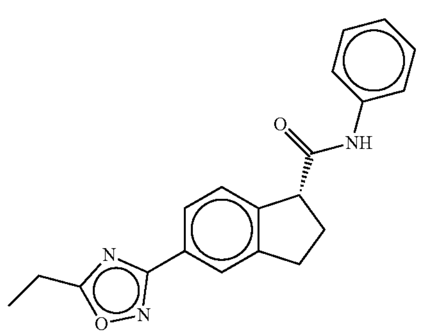 | (R)-5-(5-ethyl-1,2,4-oxadiazol-3-yl)-N-phenyl-2,3-dihydro-1H-indene-1-carboxamide |

TABLE 1-continued

| Cmpd No. | Structure | Name |
|---|---|---|
| 10 | 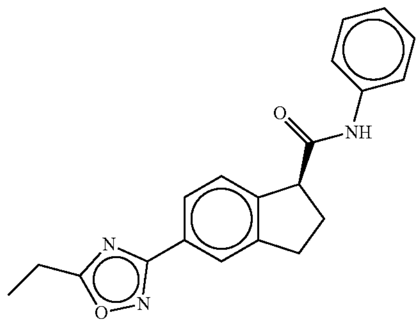 | (S)-5-(5-ethyl-1,2,4-oxadiazol-3-yl)-N-phenyl-2,3-dihydro-1H-indene-1-carboxamide |
| 11 | 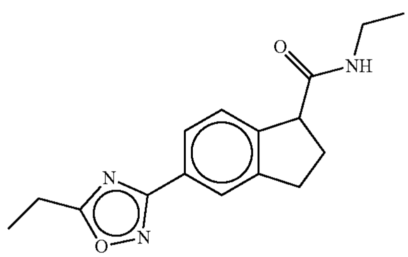 | N-ethyl-5-(5-ethyl-1,2,4-oxadiazol-3-yl)-2,3-dihydro-1H-indene-1-carboxamide |
| 12 | 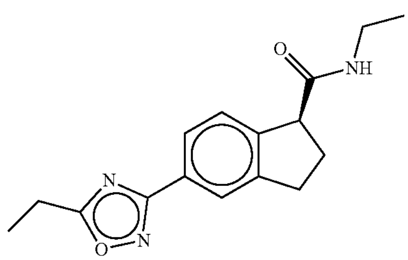 | (S)-N-ethyl-5-(5-ethyl-1,2,4-oxadiazol-3-yl)-2,3-dihydro-1H-indene-1-carboxamide |
| 13 | 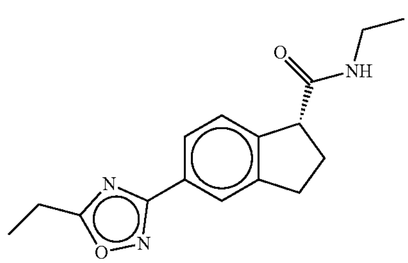 | (R)-N-ethyl-5-(5-ethyl-1,2,4-oxadiazol-3-yl)-2,3-dihydro-1H-indene-1-carboxamide |
| 14 | 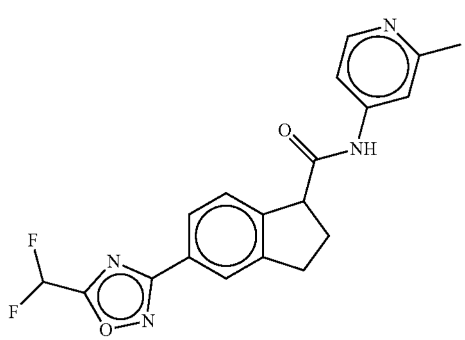 | 5-(5-(difluoromethyl)-1,2,4-oxadiazol-3-yl)-N-(2-methylpyridin-4-yl)-2,3-dihydro-1H-indene-1-carboxamide |

TABLE 1-continued

| Cmpd No. | Structure | Name |
|---|---|---|
| 15 | 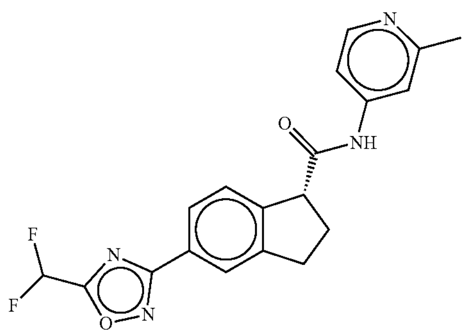 | (R)-5-(5-(difluoromethyl)-1,2,4-oxadiazol-3-yl)-N-(2-methylpyridin-4-yl)-2,3-dihydro-1H-indene-1-carboxamide |
| 16 | 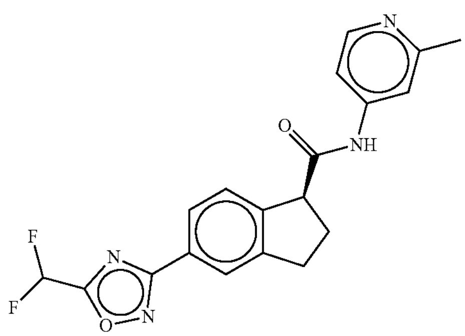 | (S)-5-(5-(difluoromethyl)-1,2,4-oxadiazol-3-yl)-N-(2-methylpyridin-4-yl)-2,3-dihydro-1H-indene-1-carboxamide |
| 17 | 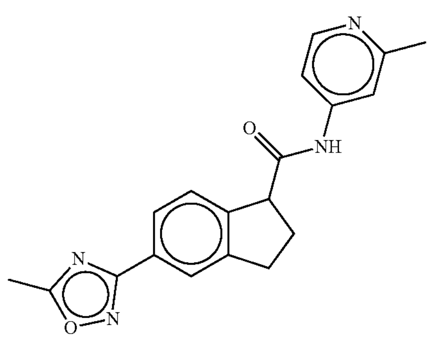 | 5-(5-methyl-1,2,4-oxadiazol-3-yl)-N-(2-methylpyridin-4-yl)-2,3-dihydro-1H-indene-1-carboxamide |
| 18 | 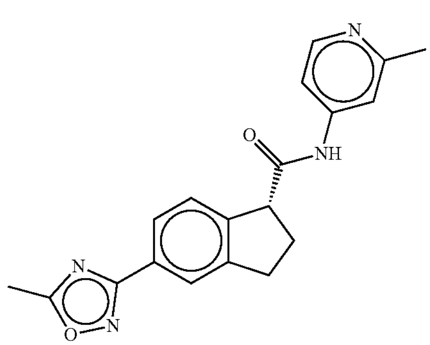 | (R)-5-(5-methyl-1,2,4-oxadiazol-3-yl)-N-(2-methylpyridin-4-yl)-2,3-dihydro-1H-indene-1-carboxamide |

TABLE 1-continued

| Cmpd No. | Structure | Name |
|---|---|---|
| 19 | 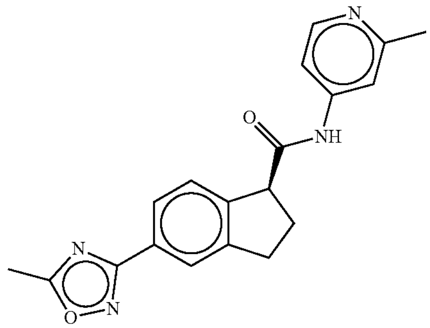 | (S)-5-(5-methyl-1,2,4-oxadiazol-3-yl)-N-(2-methylpyridin-4-yl)-2,3-dihydro-1H-indene-1-carboxamide |
| 20 | 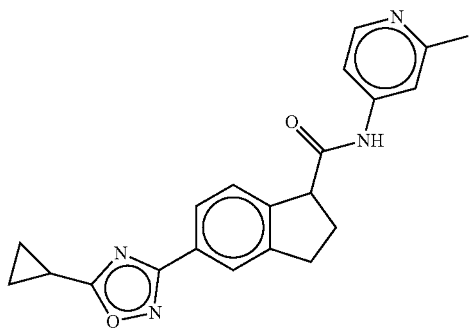 | 5-(5-cyclopropyl-1,2,4-oxadiazol-3-yl)-N-(2-methylpyridin-4-yl)-2,3-dihydro-1H-indene-1-carboxamide |
| 21 | 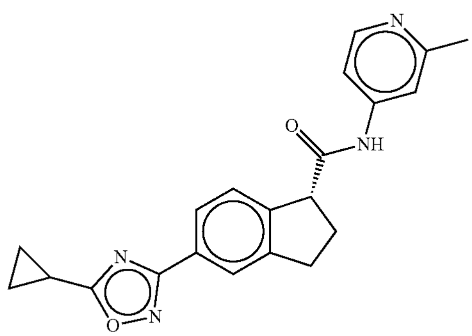 | (R)-5-(5-cyclopropyl-1,2,4-oxadiazol-3-yl)-N-(2-methylpyridin-4-yl)-2,3-dihydro-1H-indene-1-carboxamide |
| 22 | 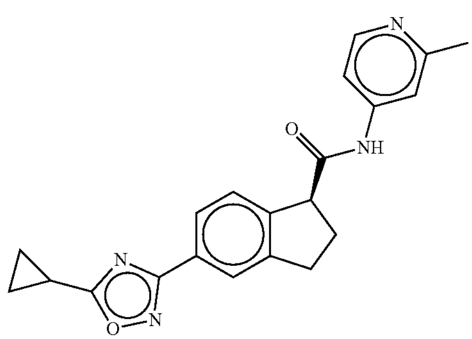 | (S)-5-(5-cyclopropyl-1,2,4-oxadiazol-3-yl)-N-(2-methylpyridin-4-yl)-2,3-dihydro-1H-indene-1-carboxamide |

TABLE 1-continued

| Cmpd No. | Structure | Name |
|---|---|---|
| 23 | 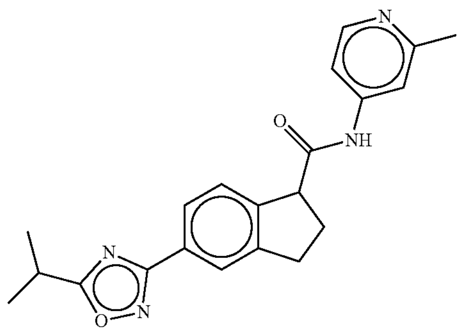 | 5-(5-isopropyl-1,2,4-oxadiazol-3-yl)-N-(2-methylpyridin-4-yl)-2,3-dihydro-1H-indene-1-carboxamide |
| 24 | 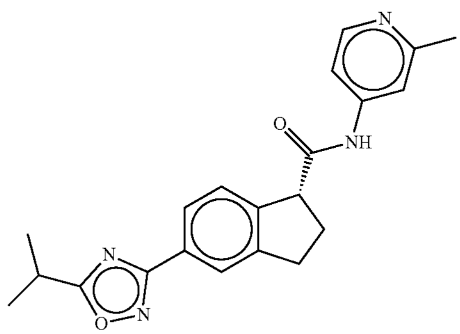 | (R)-5-(5-isopropyl-1,2,4-oxadiazol-3-yl)-N-(2-methylpyridin-4-yl)-2,3-dihydro-1H-indene-1-carboxamide |
| 25 | 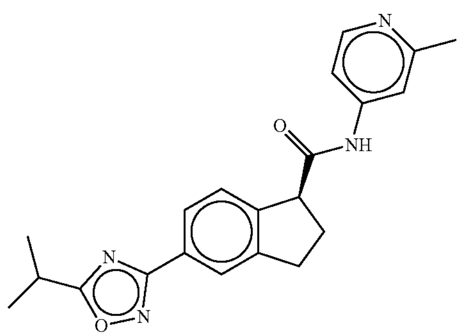 | (S)-5-(5-isopropyl-1,2,4-oxadiazol-3-yl)-N-(2-methylpyridin-4-yl)-2,3-dihydro-1H-indene-1-carboxamide |
| 26 | 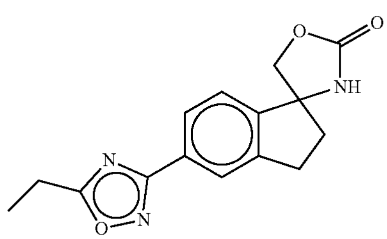 | 5-(5-ethyl-1,2,4-oxadiazol-3-yl)-2,3-dihydrospiro[indene-1,4'-oxazolidin]-2'-one |
| 27 | 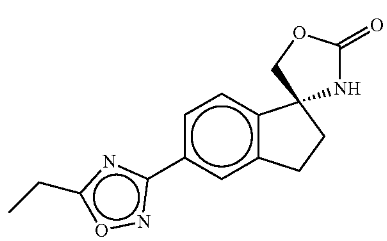 | (R)-5-(5-ethyl-1,2,4-oxadiazol-3-yl)-2,3-dihydrospiro[indene-1,4'-oxazolidin]-2'-one |

TABLE 1-continued

| Cmpd No. | Structure | Name |
|---|---|---|
| 28 | 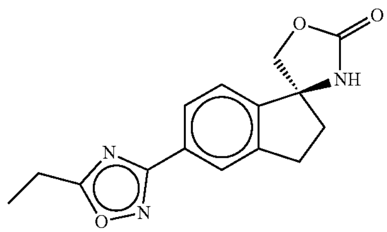 | (S)-5-(5-ethyl-1,2,4-oxadiazol-3-yl)-2,3-dihydrospiro[indene-1,4'-oxazolidin]-2'-one |
| 29 | 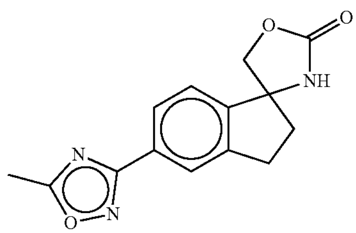 | 5-(5-methyl-1,2,4-oxadiazol-3-yl)-2,3-dihydrospiro[indene-1,4'-oxazolidin]-2'-one |
| 30 | 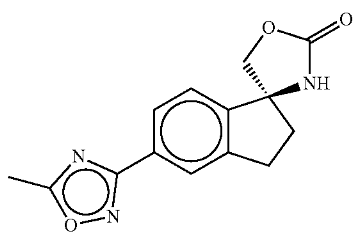 | (S)-5-(5-methyl-1,2,4-oxadiazol-3-yl)-2,3-dihydrospiro[indene-1,4'-oxazolidin]-2'-one |
| 31 | 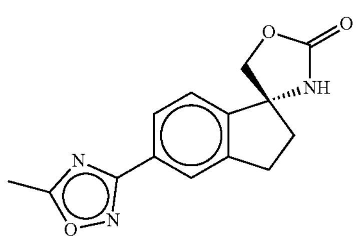 | (R)-5-(5-methyl-1,2,4-oxadiazol-3-yl)-2,3-dihydrospiro[indene-1,4'-oxazolidin]-2'-one |
| 32 | 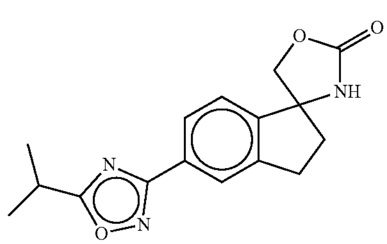 | 5-(5-isopropyl-1,2,4-oxadiazol-3-yl)-2,3-dihydrospiro[indene-1,4'-oxazolidin]-2'-one |
| 33 | 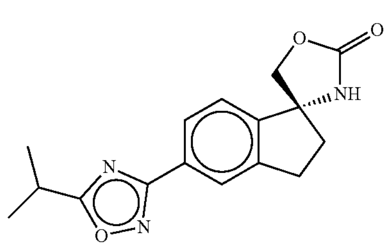 | (R)-5-(5-isopropyl-1,2,4-oxadiazol-3-yl)-2,3-dihydrospiro[indene-1,4'-oxazolidin]-2'-one |

TABLE 1-continued

| Cmpd No. | Structure | Name |
|---|---|---|
| 34 | 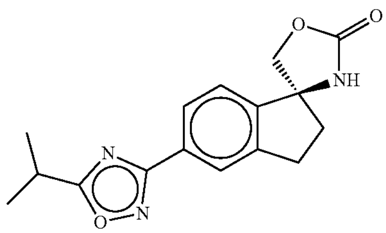 | (S)-5-(5-isopropyl-1,2,4-oxadiazol-3-yl)-2,3-dihydrospiro[indene-1,4'-oxazolidin]-2'-one |
| 35 | 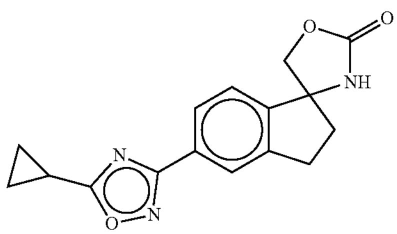 | 5-(5-cyclopropyl-1,2,4-oxadiazol-3-yl)-2,3-dihydrospiro[indene-1,4'-oxazolidin]-2'-one |
| 36 | 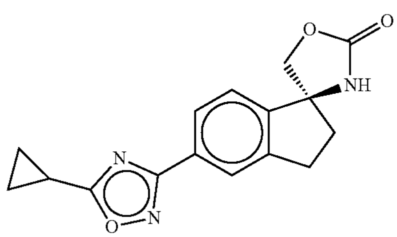 | (S)-5-(5-cyclopropyl-1,2,4-oxadiazol-3-yl)-2,3-dihydrospiro[indene-1,4'-oxazolidin]-2'-one |
| 37 | 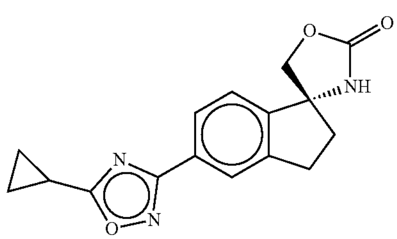 | (R)-5-(5-cyclopropyl-1,2,4-oxadiazol-3-yl)-2,3-dihydrospiro[indene-1,4'-oxazolidin]-2'-one |
| 38 | 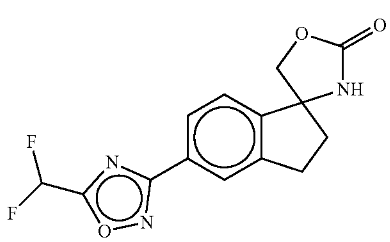 | 5-(5-(difluoromethyl)-1,2,4-oxadiazol-3-yl)-2,3-dihydrospiro[indene-1,4'-oxazolidin]-2'-one |
| 39 | 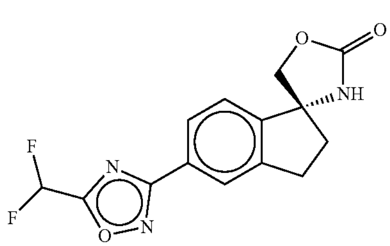 | (R)-5-(5-(difluoromethyl)-1,2,4-oxadiazol-3-yl)-2,3-dihydrospiro[indene-1,4'-oxazolidin]-2'-one |

TABLE 1-continued

| Cmpd No. | Structure | Name |
|---|---|---|
| 40 | 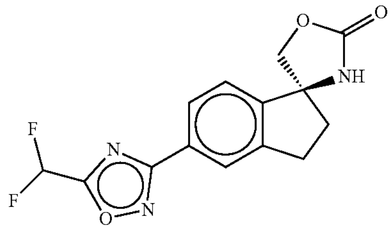 | (S)-5-(5-(difluoromethyl)-1,2,4-oxadiazol-3-yl)-2,3-dihydrospiro[indene-1,4'-oxazolidin]-2'-one |
| 41 | 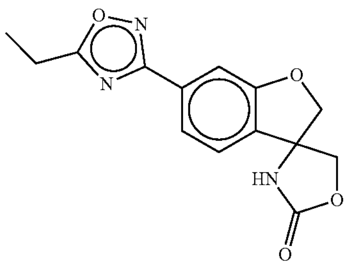 | 6-(5-ethyl-1,2,4-oxadiazol-3-yl)-2H-spiro[benzofuran-3,4'-oxazolidin]-2'-one |
| 42 | 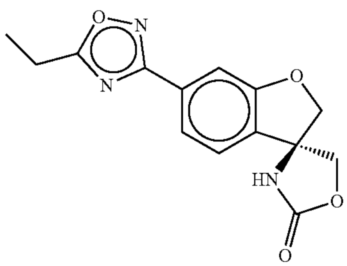 | (S)-6-(5-ethyl-1,2,4-oxadiazol-3-yl)-2H-spiro[benzofuran-3,4'-oxazolidin]-2'-one |
| 43 | 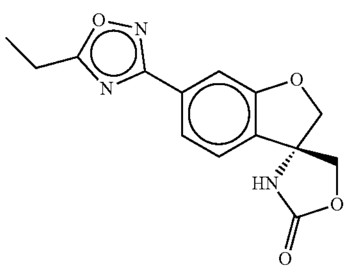 | (R)-6-(5-ethyl-1,2,4-oxadiazol-3-yl)-2H-spiro[benzofuran-3,4'-oxazolidin]-2'-one |

In some variations, any of the compounds described herein, such as a compound of Formula (I), (Ia), (Ib), (Ic), (Id), (Ie), or (If), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (Ia), (Ib), (Ic), (Id), (Ie), or (If), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of X, $R^1$, $R^2$, $R^3$ and $R^a$ provided herein can be combined with every other variation or embodiment of X, $R^1$, $R^2$, $R^3$ and $R^a$ as if each combination had been individually and specifically described.

As used herein, when any variable occurs more than one time in a chemical formula, its definition on each occurrence is independent of its definition at every other occurrence.

Formula (I) includes all subformulae thereof. For example, Formula (I) includes compounds of Formula (Ia), (Ib), (Ic), (Id), (Ie), and (If).

The compound names provided herein, including in Table 1, are provided by ChemBioDraw Professional 15.0.0.106. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (Ia), (Ib), (Ic), (Id), (Ie), or (If), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

The compounds and pharmaceutical compositions herein may be used to treat or prevent a disease or condition in an individual or subject.

When used in a prophylactic manner, the compounds disclosed and/or described herein may prevent a disease or disorder from developing in an individual or subject at risk of developing the disease or disorder, or lessen the extent of a disease or disorder that may develop.

Without being bound by theory, the compounds and pharmaceutical compositions disclosed herein are believed to act by inhibiting myosin. This inhibition potentially decreases the number of independent myosin heads interacting with actin filaments reducing the amount of contraction. Reducing contraction of cardiac muscle can be important for the treatment of heart diseases in which over-contraction is an issue. In some embodiments, provided are methods of treating or preventing heart disease in an individual or subject, comprising administering to the individual or subject in need thereof a compound of Formula (I), (Ia), (Ib), (Ic), (Id), (Ie), or (If), or a compound of Table 1, or a pharmaceutically acceptable salt thereof. In some embodiments, provided are methods of treating or preventing heart disease in a subject in need thereof comprising administering to the subject a therapeutically effective amount of at least one chemical entity as described herein. In some embodiments, provided are methods of treating heart disease in a subject in need thereof comprising administering to the subject a therapeutically effective amount of at least one chemical entity as described herein. In some embodiments, provided are methods of treating an established or diagnosed heart disease in a subject in need thereof comprising administering to the subject a therapeutically effective amount of at least one chemical entity as described herein. In some embodiments, provided are methods of preventing heart disease in a subject in need thereof comprising administering to the subject a therapeutically effective amount of at least one chemical entity as described herein.

Also provided herein is the use of a compound of Formula (I), (Ia), (Ib), (Ic), (Id), (Ie), or (If), or a compound of Table 1, or a pharmaceutically acceptable salt thereof in the manufacture of a medicament for treatment of a heart disease in a subject. In some aspects, provided is a compound or composition as described herein for use in a method of treatment of the human or animal body by therapy. In some embodiments, provided herein are compounds of Formula (I), (Ia), (Ib), (Ic), (Id), (Ie), or (If), or a compound of Table 1, or a pharmaceutically acceptable salt thereof, for use in a method of treatment of the human or animal body by therapy. In some embodiments, provided herein are compounds of Formula (I), (Ia), (Ib), (Ic), (Id), (Ie), or (If), or a compound of Table 1, or a pharmaceutically acceptable salt thereof, for use in treating or preventing heart disease. In some embodiments, provided herein are compounds of Formula (I), (Ia), (Ib), (Ic), (Id), (Ie), or (If), or a compound of Table 1, or a pharmaceutically acceptable salt thereof, for use in treating heart disease. In some embodiments, provided herein are compounds of Formula (I), (Ia), (Ib), (Ic), (Id), (Ie), or (If), or a compound of Table 1, or a pharmaceutically acceptable salt thereof, for use in treating an established or diagnosed heart disease. In other embodiments, provided herein are compounds of Formula (I), (Ia), (Ib), (Ic), (Id), (Ie), or (If), or a compound of Table 1, or a pharmaceutically acceptable salt thereof, for use in preventing heart disease. In some embodiments, provided herein are compounds of Formula (I), (Ia), (Ib), (Ic), (Id), (Ie), or (If), or a compound of Table 1, or a pharmaceutically acceptable salt thereof, for use in treating a disease or condition associated with HCM. In some embodiments, provided herein are compounds of Formula (I), (Ia), (Ib), (Ic), (Id), (Ie), or (If), or a compound of Table 1, or a pharmaceutically acceptable salt thereof, for use in treating a disease or condition associated with secondary left ventricular wall thickening. In some embodiments, provided herein are compounds of Formula (I), (Ia), (Ib), (Ic), (Id), (Ie), or (If), or a compound of Table 1, or a pharmaceutically acceptable salt thereof, for use in ameliorating a symptom associated with heart disease. In other embodiments, provided herein are compounds of Formula (I), (Ia), (Ib), (Ic), (Id), (Ie), or (If), or a compound of Table 1, or a pharmaceutically acceptable salt thereof, for use in reducing the risk of a symptom associated with heart disease. In other embodiments, provided herein are compounds of Formula (I), (Ia), (Ib), (Ic), (Id), (Ie), or (If), or a compound of Table 1, or a pharmaceutically acceptable salt thereof, for use in treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis. In certain embodiments, provided herein are compounds of Formula (I), (Ia), (Ib), (Ic), (Id), (Ie), or (If), or a compound of Table 1, or a pharmaceutically acceptable salt thereof, for use in treating a disease or condition associated with small left ventricular cavity and cavity obliteration, hyperdynamic left ventricular contraction, myocardial ischemia, or cardiac fibrosis. In some embodiments, provided herein are compounds of Formula (I), (Ia), (Ib), (Ic), (Id), (Ie), or (If), or a compound of Table 1, or a pharmaceutically acceptable salt thereof, for use in treating muscular dystrophies. In some embodiments, provided herein are compounds of Formula (I), (Ia), (Ib), (Ic), (Id), (Ie), or (If), or a compound of Table 1, or a pharmaceutically acceptable salt thereof, for use in treating a glycogen storage disease. In other embodiments, provided herein are compounds of Formula (I), (Ia), (Ib), (Ic), (Id), (Ie), or (If), or a compound of Table 1, or a pharmaceutically acceptable salt thereof, for use in modulating the cardiac sarcomere, such as inhibiting the cardiac sarcomere. In yet other embodiments, provided herein are compounds of Formula (I), (Ia), (Ib), (Ic), (Id), (Ie), or (If), or a compound of Table 1, or a pharmaceutically acceptable salt thereof, for use in potentiating cardiac myosin.

In some embodiments, the subject is a mammal. In some embodiments, the subject is a mouse, rat, dog, cat, pig, sheep, horse, cow, or human. In some embodiments, the subject is a human. In some embodiments, the subject has an established or diagnosed heart disease. In some embodiments, the subject has established or diagnosed hypertrophic cardiomyopathy (HCM). In some embodiments, the subject is at risk for developing heart disease. In some embodiments, the subject has a mutation that increases risk for heart disease. In some embodiments, the subject has a mutation that increases risk for hypertrophic cardiomyopathy (HCM). In some embodiments, the mutation is a sarcomeric mutation. In some embodiments, the mutation is a mutation in myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, muscle LIM protein (MLP), or protein kinase AMP-activated non-catalytic subunit gamma 2 (PRKAG2). In some embodiments, the mutation is a mutation in MHC-β. In some embodiments, the subject has established or diagnosed hypertrophic cardiomyopathy without a confirmed genetic etiology.

In some embodiments, the subject has a high risk of progressive symptoms. In some embodiments, the subject has a high risk of atrial fibrillation, ventricular tachyarrhythmias, stroke, and/or sudden death. In some embodiments, the subject has a reduced exercise capacity. In some embodiments, the reduced exercise capacity is as compared to an age-matched control population. In some embodiments, the subject is eligible for surgical intervention or percutaneous ablation to treat the heart disease.

In some embodiments, the heart disease is hypertrophic cardiomyopathy (HCM). In some embodiments, the heart disease is obstructive HCM. In some embodiments, the heart disease is nonobstructive HCM. In some embodiments, the HCM is associated with a sarcomeric mutation. In some embodiments, the HCM is associated with a non-sarcomeric mutation. In some embodiments, the heart disease is obstructive or nonobstructive HCM caused by sarcomeric and/or non-sarcomeric mutations. In some embodiments, the sarcomeric mutation is a mutation in a myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, or muscle LIM protein (MLP). In some embodiments, the sarcomeric mutation is a mutation in MHC-β. In some embodiments, the non-sarcomeric mutation is a mutation in protein kinase AMP-activated non-catalytic subunit gamma 2 (PRKAG2).

In some embodiments, provided herein are methods of treating a disease or condition associated with HCM, comprising administering to the individual or subject in need thereof a compound of Formula (I), (Ia), (Ib), (Ic), (Id), (Ie), or (If), or a compound of Table 1, or a pharmaceutically acceptable salt thereof. In some embodiments, the disease or condition is Fabry's Disease, Danon Disease, mitochondrial cardiomyopathies, or Noonan Syndrome.

Also provided herein is the use of a compound of Formula (I), (Ia), (Ib), (Ic), (Id), (Ie), or (If), or a compound of Table 1, or a pharmaceutically acceptable salt thereof in the manufacture of a medicament for treatment of a disease or condition associated with HCM.

In some embodiments, the heart disease is heart failure with preserved ejection fraction (HFpEF). In some embodiments, the heart disease is diastolic dysfunction. In some embodiments, the heart disease is cardiomyopathy. In some embodiments, the heart disease is primary or secondary restrictive cardiomyopathy. In some embodiments, the heart disease is condition or symptoms caused by coronary artery disease. In some embodiments, the heart disease is myocardial infarction or angina pectoris. In some embodiments, the heart disease is left ventricular outflow tract obstruction. In some embodiments, the heart disease is hypertensive heart disease. In some embodiments, the heart disease is congenital heart disease. In some embodiments, the heart disease is cardiac ischemia and/or coronary heart disease. In some embodiments, the heart disease is diabetic heart disease. In other embodiments, the heart disease is congestive heart failure. In some embodiments, the heart disease is right heart failure. In other embodiments, the heart disease is cardio-renal syndrome. In some embodiments, the heart disease is infiltrative cardiomyopathy. In some embodiments, the heart disease is a condition that is or is related to cardiac senescence or diastolic dysfunction due to aging. In some embodiments, the heart disease is a condition that is or is related to left ventricular hypertrophy and/or concentric left ventricular remodeling.

In some embodiments, the provided are methods of treating a disease or condition associated with secondary left ventricular wall thickening in an individual or subject, comprising administering to the individual or subject in need thereof a compound of Formula (I), (Ia), (Ib), (Ic), (Id), (Ie), or (If), or a compound of Table 1, or a pharmaceutically acceptable salt thereof. In some embodiments, the disease is hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, or Pompe disease.

Also provided herein is the use of a compound of Formula (I), (Ia), (Ib), (Ic), (Id), (Ie), or (If), or a compound of Table 1, or a pharmaceutically acceptable salt thereof in the manufacture of a medicament for treatment of a disease or condition associated with secondary left ventricular wall thickening.

In some embodiments, provided are methods of ameliorating a symptom associated with heart disease in a subject, comprising administering to the individual or subject in need thereof a compound of Formula (I), (Ia), (Ib), (Ic), (Id), (Ie), or (If), or a compound of Table 1, or a pharmaceutically acceptable salt thereof, wherein the symptom is one or more selected from poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of reducing the risk of a symptom associated with heart disease in a subject, comprising administering to the individual or subject in need thereof a compound of Formula (I), (Ia), (Ib), (Ic), (Id), (Ie), or (If), or a compound of Table 1, or a pharmaceutically acceptable salt thereof, wherein the symptom is one or more selected from sudden cardiac death, poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis in an individual or subject, comprising administering to the individual or subject in need thereof a compound of Formula (I), (Ia), (Ib), (Ic), (Id), (Ie), or (If), or a compound of Table 1, or a pharmaceutically acceptable salt thereof.

In some embodiments, provided are methods of treating a disease or condition associated with small left ventricular cavity and cavity obliteration, hyperdynamic left ventricular contraction, myocardial ischemia, or cardiac fibrosis in an individual or subject, comprising administering to the individual or subject in need thereof a compound of Formula (I), (Ia), (Ib), (Ic), (Id), (Ie), or (If), or a compound of Table 1, or a pharmaceutically acceptable salt thereof.

Also provided herein is the use of a compound of Formula (I), (Ia), (Ib), (Ic), (Id), (Ie), or (If), or a compound of Table 1, or a pharmaceutically acceptable salt thereof in the manufacture of a medicament for treatment of a disease or condition associated with small left ventricular cavity and cavity obliteration, hyperdynamic left ventricular contraction, myocardial ischemia, or cardiac fibrosis.

In some embodiments, the provided are methods of treating muscular dystrophies in an individual or subject (e.g., Duchenne muscular dystrophy), comprising administering to the individual or subject in need thereof a compound of Formula (I), (Ia), (Ib), (Ic), (Id), (Ie), or (If), or a compound of Table 1, or a pharmaceutically acceptable salt thereof. Also provided herein is the use of a compound of Formula (I), (Ia), (Ib), (Ic), (Id), (Ie), or (If), or a compound of Table 1, or a pharmaceutically acceptable salt thereof in the manufacture of a medicament for treatment of muscular dystrophies (e.g., Duchenne muscular dystrophy).

In some embodiments, provided are methods of treating a glycogen storage disease in an individual or subject, comprising administering to the individual or subject in need thereof a compound of Formula (I), (Ia), (Ib), (Ic), (Id), (Ie), or (If), or a compound of Table 1, or a pharmaceutically acceptable salt thereof. Also provided herein is the use of a compound of Formula (I), (Ia), (Ib), (Ic), (Id), (Ie), or (If), or a compound of Table 1, or a pharmaceutically acceptable salt thereof in the manufacture of a medicament for treatment of a glycogen storage disease.

Also provided are methods for modulating the cardiac sarcomere in an individual or subject which method comprises administering to an individual or subject in need thereof a therapeutically effective amount of at least one chemical entity as described herein. In some embodiments, provided are methods of inhibiting the cardiac sarcomere, comprising contacting the cardiac sarcomere with at least one chemical entity as described herein, such as a compound of Formula (I), (Ia), (Ib), (Ic), (Id), (Ie), or (If), or a compound of Table 1, or a pharmaceutically acceptable salt thereof. Additionally provided herein is the use of at least one chemical entity as described herein, such as a compound of Formula (I), (Ia), (Ib), (Ic), (Id), (Ie), or (If), or a compound of Table 1, or a pharmaceutically acceptable salt thereof in the manufacture of a medicament for inhibiting the cardiac sarcomere of an individual or subject.

Also provided are methods for potentiating cardiac myosin in an individual or subject which method comprises administering to an individual or subject in need thereof a therapeutically effective amount of at least one chemical entity as described herein such as a compound of Formula (I), (Ia), (Ib), (Ic), (Id), (Ie), or (If), or a compound of Table 1, or a pharmaceutically acceptable salt thereof. Additionally provided herein is the use of at least one chemical entity as described herein, such as a compound of Formula (I), (Ia), (Ib), (Ic), (Id), (Ie), or (If), or a compound of Table 1, or a pharmaceutically acceptable salt thereof in the manufacture of a medicament for potentiating cardiac myosin in an individual or subject.

In some embodiments, the methods provided herein further comprise monitoring the effectiveness of the treatment. Examples of indicators include, but are not limited to improvement in one or more of the following: New York Heart Association (NYHA) Functional Classification, exercise capacity, cardiac elasticity, diastolic left ventricular relaxation, left atrial pressure, paroxysmal or permanent atrial fibrillation, left atrial and pulmonary capillary wedge pressures, left ventricular diastolic pressures, syncope, ventricular relaxation during diastole, ventricular fibrosis, left ventricular hypertrophy, left ventricular mass, left ventricular wall thickness, left ventricular mid-cavity obstruction systolic anterior motion of mitral valve, left ventricular outflow tract obstruction, chest pain, exertional dyspnea, pre-syncope, abnormal exercise capacity, and fatigue. These indicators can be monitored by techniques known in the art including self-reporting; ECG, including ambulatory ECG; echocardiography; cardiac MRI; CT; biopsy; cardiopulmonary exercise testing (CPET); and actigraphy.

In some embodiments, the compound reduces the contractility of a cardiomyocyte. In some embodiments, the compound reduces the contractility of a cardiomyocyte by greater than 40%, such as greater than 45%, 50%, 60%, 70%, 80%, or 90%. In some embodiments, the compound reduced the contractility of a cardiomyocyte 40%-90%, such as 40%-80%, 40%-70%, 50%-90%, 50%-80% or 50%-70%. In some embodiments, the compound does not significantly alter calcium transients in the cardiomyocyte. In some embodiments, the compound decreases the ATPase activity in a cardiomyocyte. Methods of measuring contractility, ATPase activity, and calcium transients are known in the art, for example, by calcium labeling, electrophysiological recordings, and microscopic imaging. In some embodiments, the compound does not significantly inhibit or induce a cytochrome P450 (CYP) protein.

In some embodiments, the subject has a left ventricular wall that is thicker than normal prior to treatment. In some embodiments, the subject has a left ventricular wall thickness that is greater than 15 mm, such as greater than 18 mm, 20 mm, 22 mm, 25 mm, or 30 mm prior to treatment. In some embodiments, the left ventricular wall thickness is reduced by greater than 5%, such as greater than 8%, 10%, 12%, 15%, 20%, or 30% following treatment. Left ventricular wall thickness can be measured by methods known in the art, such as by echocardiography, CT scan, or a cardiac MRI.

In some embodiments, the subject has abnormal cardiac fibrosis prior to treatment. In some embodiments, the abnormal cardiac fibrosis is reduced by greater than 5%, such as greater than 8%, 10%, 12%, 15%, 20%, or 30% following treatment. Cardiac fibrosis can be measured by methods known in the art, such as by biopsy or a cardiac MRI.

In some embodiments, the subject has reduced exercise capacity prior to treatment. In some embodiments, the exercise capacity of the subject is increased by greater than 5%, such as greater than 8%, 10%, 12%, 15%, 20% or 30% following treatment. In some embodiments, the exercise capacity is measured by cardiopulmonary exercise testing (CPET). CPET measures changes in oxygen consumption ($VO_2$ max). Methods of measuring CPET and $VO_2$ max are well known in the art (Malhotra et al., JACC: Heart Failure, 2016, 4(8): 607-616; Guazzi et al., J Amer College Cardiol, 2017, 70 (13): 1618-1636; Rowin et al., JACC: Cariovasc Imaging, 2017, 10(11):1374-1386). In some embodiments, $VO_2$ max is improved by more than 1 mL/kg/m$^2$, such as more than 1.2 mL/kg/m$^2$, 1.4 mL/kg/m$^2$, 1.5 mL/kg/m$^2$, 1.7 mL/kg/m$^2$, 2 mL/kg/m$^2$, 2.2 mL/kg/m$^2$, 2.5 mL/kg/m$^2$, 3 mL/kg/m$^2$, 3.2 mL/kg/m$^2$, or 3.5 mL/kg/m$^2$ following treatment.

In some embodiments, the subject has a New York Heart Association (NYHA) Functional Classification of II, III, or IV prior to treatment. In some embodiments, the subject has a New York Heart Association (NYHA) Functional Classification of III or IV prior to treatment. In some embodiments, the subject has a New York Heart Association (NYHA) Functional Classification of IV prior to treatment. In some embodiments, the subject remains in the same NYHA functional class or has a reduced NYHA functional class following treatment.

In some embodiments, $VO_2$ max is improved by more than 1 ml/kg/m$^2$, such as more than 1.2 mL/kg/m$^2$, 1.4 mL/kg/m$^2$, 1.5 mL/kg/m$^2$, 1.7 mL/kg/m$^2$, or 2 mL/kg/m$^2$ and the subject has a reduced NYHA functional class following treatment. In some embodiments, $VO_2$ max is improved by more than 2.5 mL/kg/m$^2$, 3 mL/kg/m$^2$, 3.2 mL/kg/m$^2$, or 3.5 mL/kg/m$^2$ and the subject remains in the same NYHA functional class or has a reduced NYHA functional class following treatment.

In some embodiments, daily function and/or activity level of the subject is improved following treatment. Improved daily function and/or activity level may be measured, for example, by journaling or actigraphy, such as a FitBit or FitBit-like monitors.

In some embodiments, the subject has one or more of decreased shortness of breath, decreased chest pain, decreased arrhythmia burden, such as atrial fibrillation and ventricular arrhythmias, decreased incidence of heart failure, and decreased ventricular outflow obstruction following treatment.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

The compounds and compositions described and/or disclosed herein may be combined with one or more other therapies to treat a heart disease, such as HCM or HFpEF. In some embodiments, the one or more therapies include therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors). In some embodiments, the one or more therapies include therapies that improve cardiac function by stimulating cardiac contractility (e.g., positive inotropic agents, such as the β-adrenergic agonist dobutamine or the phosphodiesterase inhibitor milrinone). In other embodiments, the one or more therapies include therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The compounds and compositions described and/or disclosed herein may be combined with one or more other therapies to treat HCM or HFpEF. In some embodiments, the compounds and/compositions may be combined with a β-blocker, verapamil, and/or disopyramide.

General Synthetic Methods

Compounds of Formula (I), (Ia), (Ib), (Ic), (Id), (Ie), and (If), will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (Ia), (Ib), (Ic), (Id), (Ie), and (If).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (Ia), (Ib), (Ic), (Id), (Ie), and (If), or any variation thereof. Other compounds described herein may be prepared by similar methods.

In some embodiments, compounds provided herein may be synthesized according to Scheme 1.

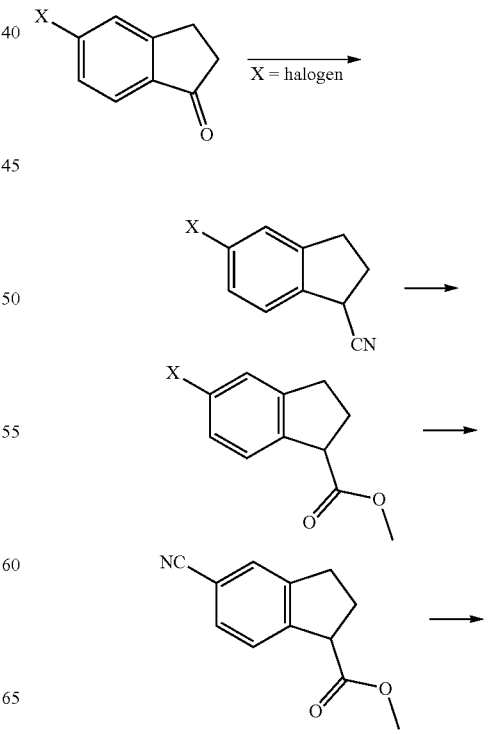

Scheme 1

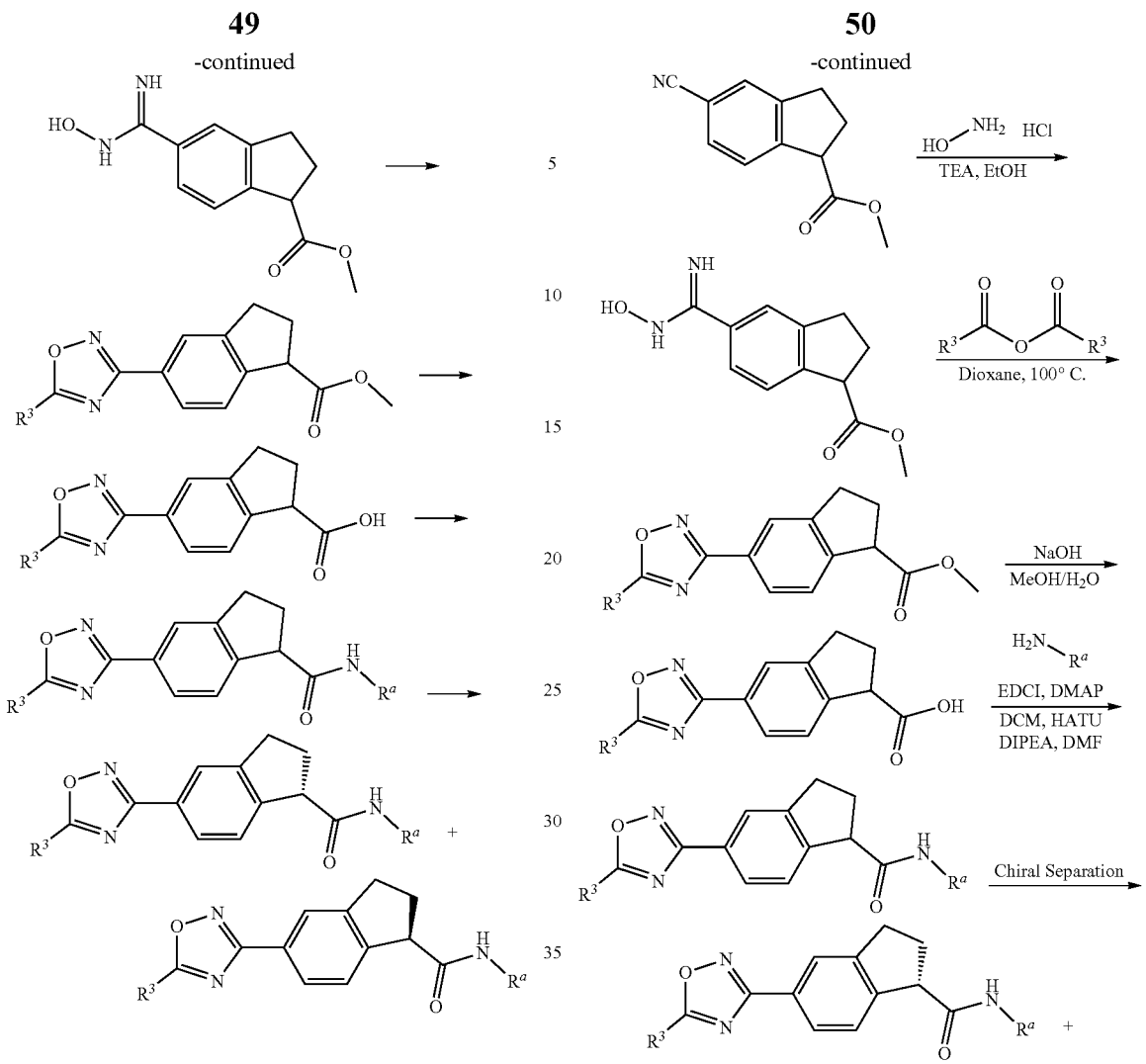
An exemplary embodiment of the preparative method in Scheme 1 is shown in Scheme 1a.
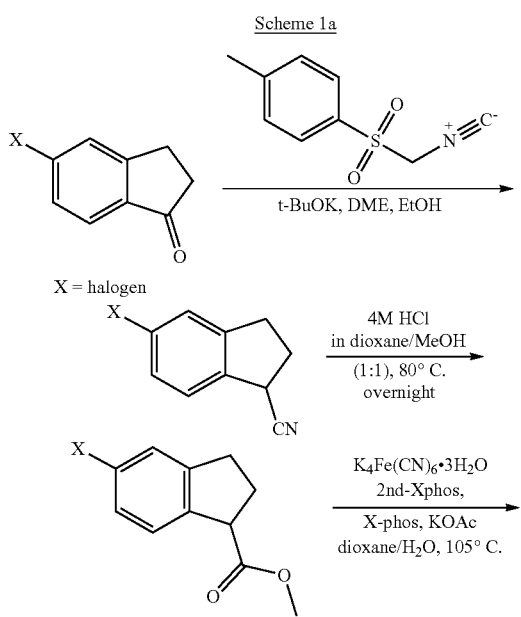
In some embodiments, compounds provided herein may be synthesized according to Scheme 2.
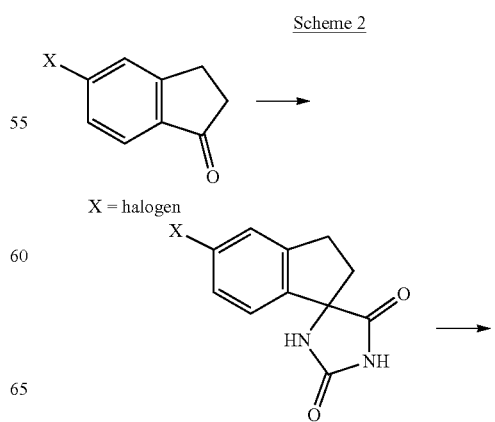

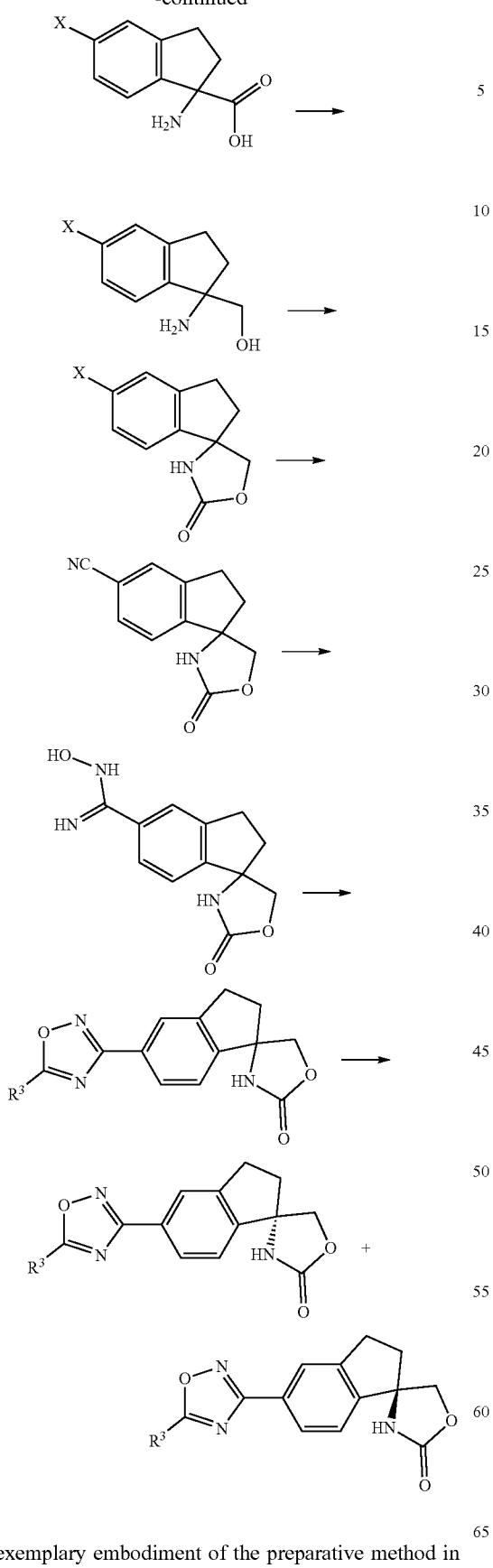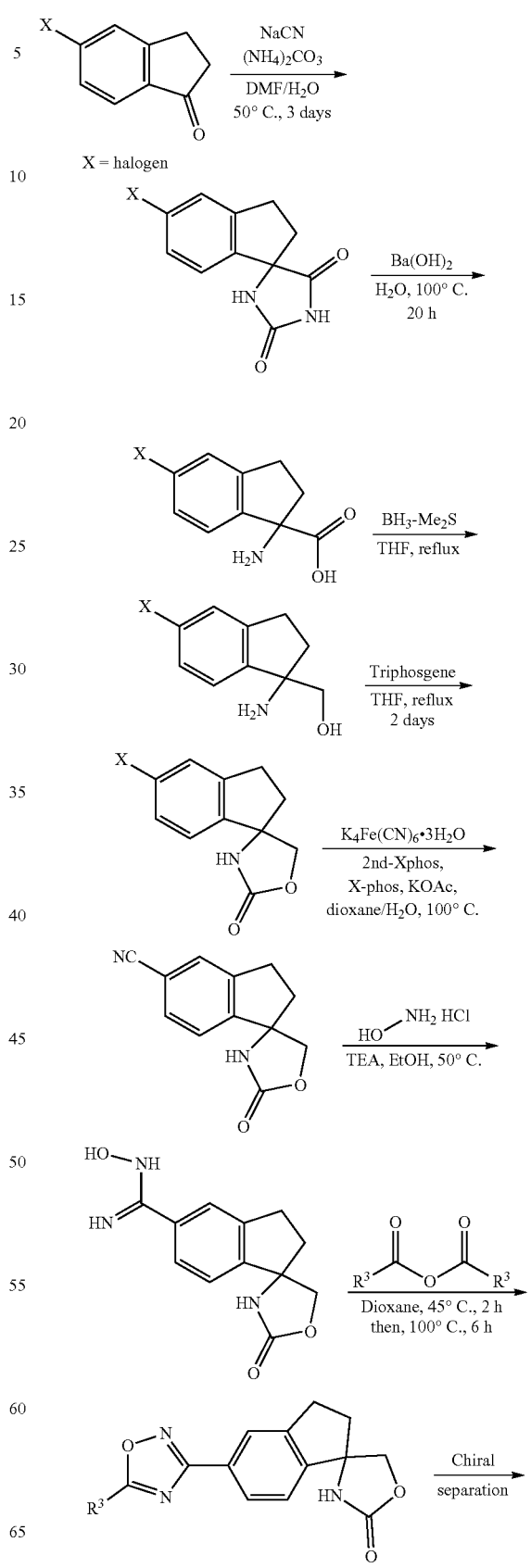
An exemplary embodiment of the preparative method in Scheme 2 is shown in Scheme 2a.

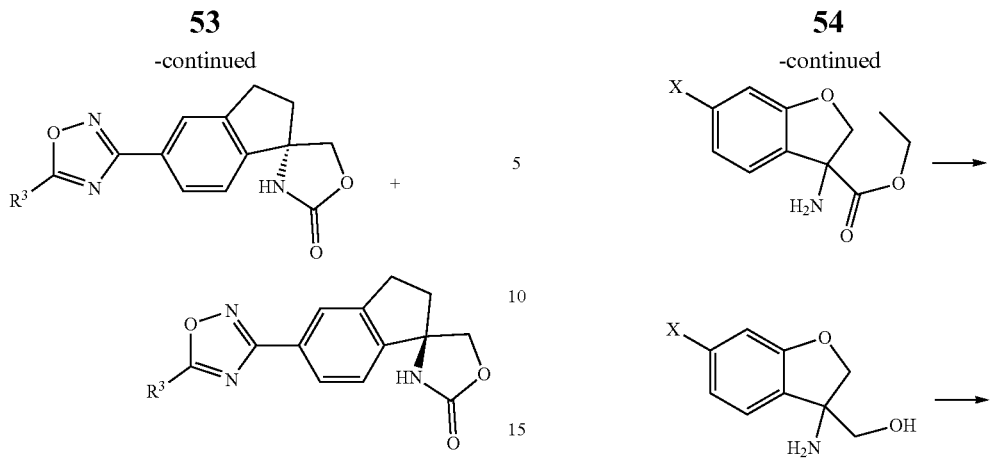
In some embodiments, compounds provided herein may be synthesized according to Scheme 3.
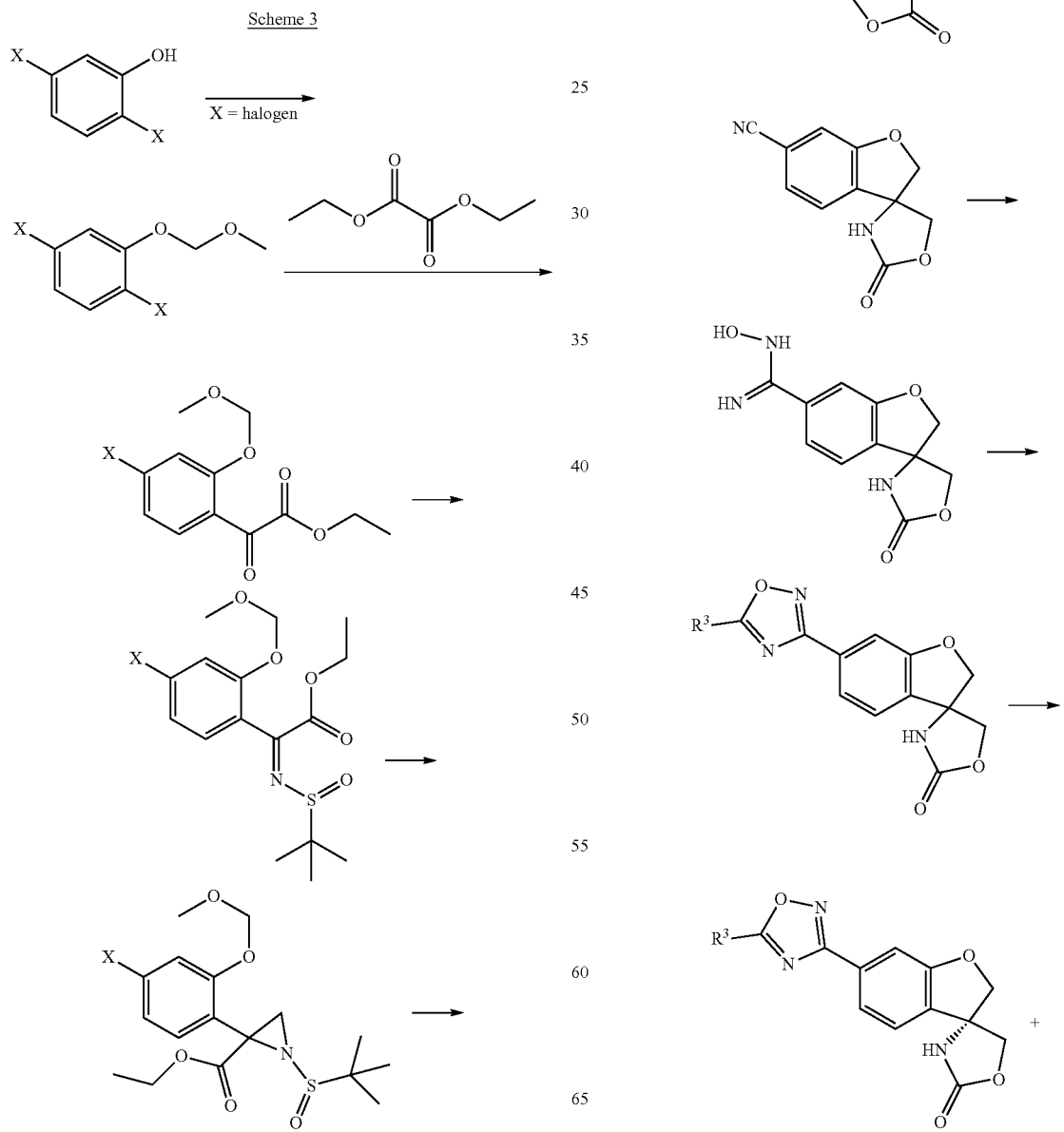

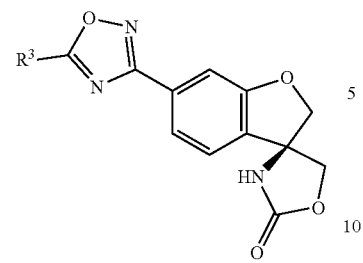
An exemplary embodiment of the preparative method in Scheme 3 is shown in Scheme 3a.
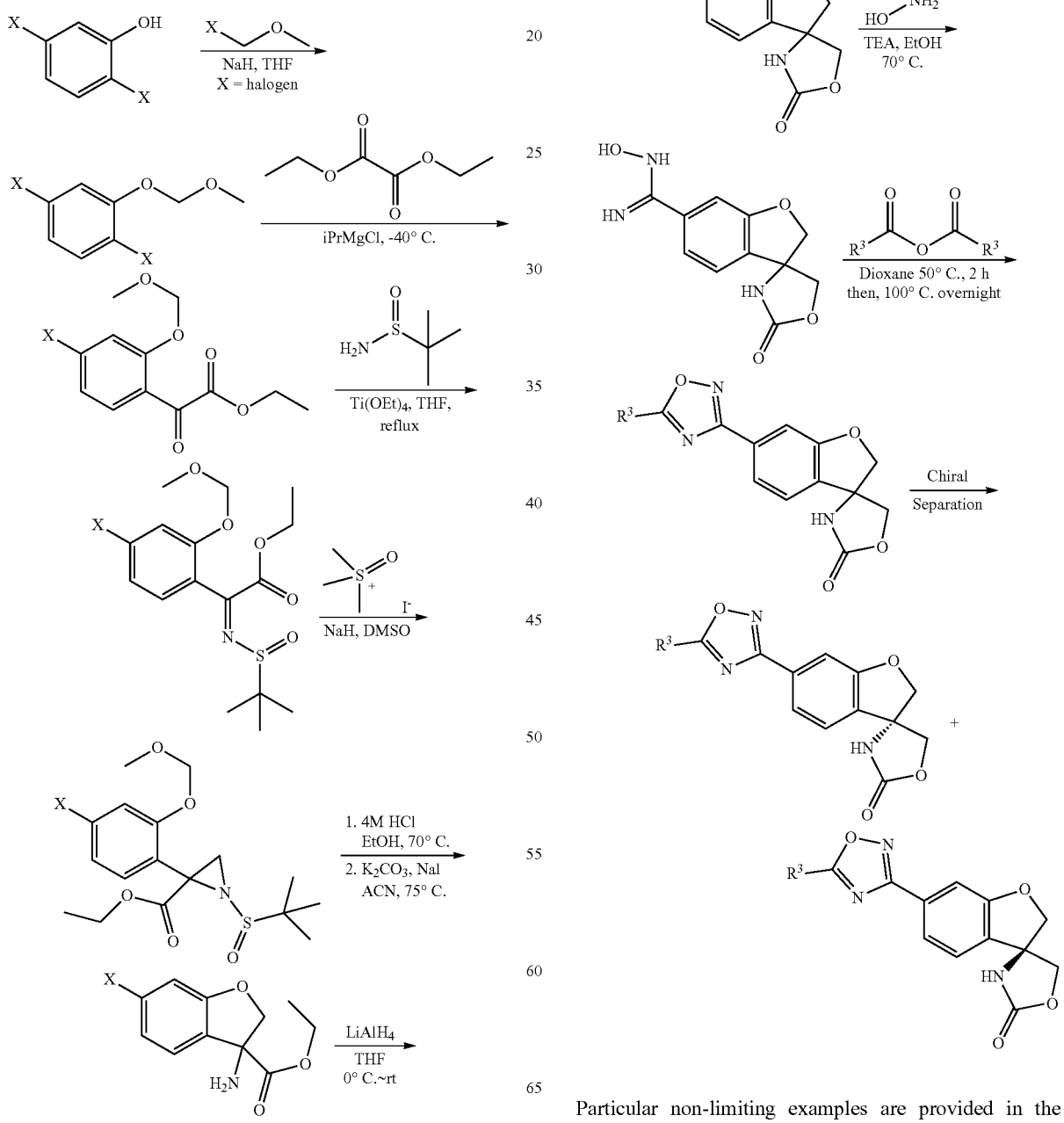
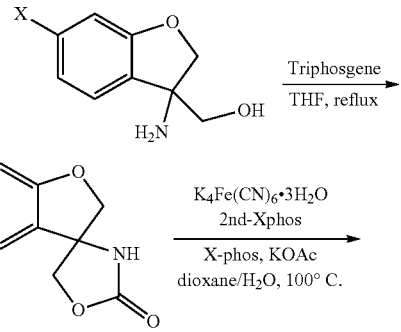
Particular non-limiting examples are provided in the Example section below.

EXAMPLES

The following examples are offered to illustrate but not to limit the compositions, uses, and methods provided herein. The compounds are prepared using the general methods described above.

The following abbreviations are used throughout the Examples: IPA (isopropyl amine), DEA (diethylamine), MtBE (methyl tert-butyl ether), RT (retention time), TEA (trimethylamine), DME (dimethoxyethane), Me (methyl), Et (ethyl), iPr (isopropyl), DCM (dichloromethane), MeOH (methanol), (Boc)$_2$O (di-tert-butyl dicarbonate), EA (ethyl acetate), DMSO (dimethyl sulfoxide), PE (petroleum ether, DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-hydroxy-7-azabenzotriazole), HOBt (hydroxybenzotriazole), EDCI (1-ethyl-3-(3-dimethylaminopropyl)carbodiimide), DMAP (dimethylaminopyridine), EtOH (ethanol), iPrOH (propan-2-ol), ACN (acetonitrile), TFA (trifluoroacetic acid), DPPA (diphenylphosphoryl azide), DBU (1,8-diazabicyclo(5.4.0)undec-7-ene), THF (tetrahydrofuran), PPh$_3$ (triphenylphosphine), SM (starting material), Hex (hexane), NCS (N-chlorosuccinimide), r.t. (room temperature), DCE (dichloroethane), FA (formic acid), CHCl$_3$ (chloroform), BnBr (benzyl bromide), HCl (hydrogen chloride), equiv (equivalent), t-BuOK (potassium tert-butoxide), KOAc (potassium acetate), and DSC (bis(2,5-dioxopyrrolidin-1-yl) carbonate).

Example 1

Synthesis of Compound 2

1. Synthesis of Intermediate 1-2

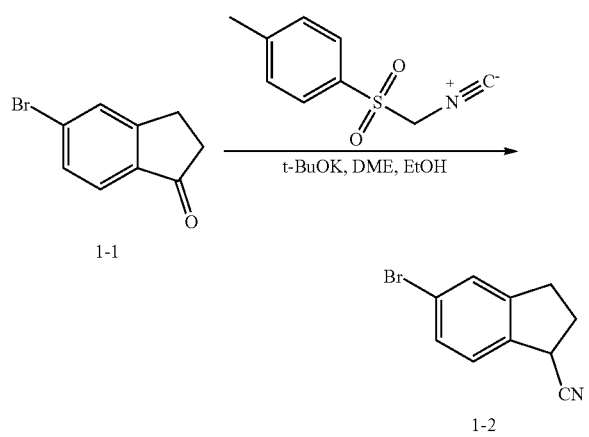

To a stirred solution of 1-(isocyanomethane)sulfonyl-4-methylbenzene (30.2 g, 154.7 mmol, 1.31 equiv) in DME (500 mL) at r.t. were added EtOH (18 mL, 308.7 mmol, 2.61 equiv), 5-bromo-2,3-dihydro-1H-inden-1-one (25 g, 118.5 mmol, 1 equiv) in portions. To the above mixture cooled to 0° C. with an ice bath was added t-BuOK (33.3 g, 296.8 mmol, 2.5 equiv) in portions over 10 min and the ice bath temperature was kept under 11° C. The mixture was stirred for 30 min while maintaining the ice bath temperature under 12° C. with addition of ice. The precipitated solid was filtered and washed with DME (100 mL) three times. The filtrate was diluted with EA (400 mL), washed with brine (300 mL) three times, dried over Na$_2$SO$_4$, concentrated under reduced pressure and purified by silica gel column chromatography, eluting with PE/EA (10:1), to give 14 g (53.2%) of 5-bromo-2,3-dihydro-1H-indene-1-carbonitrile as a brown oil.

2. Synthesis of Intermediate 1-3

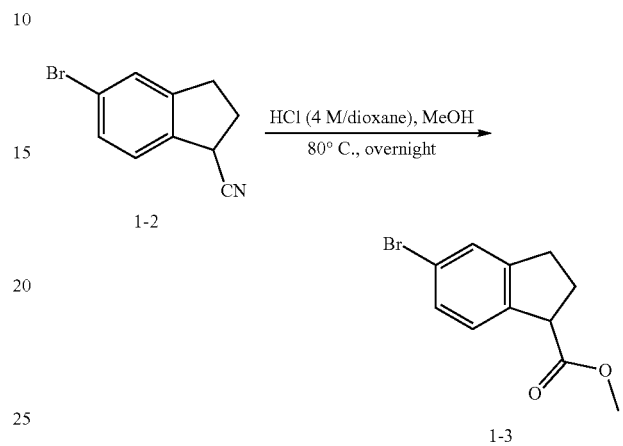

To a stirred solution of 5-bromo-2,3-dihydro-1H-indene-1-carbonitrile (14.0 g, 63.0 mmol, 1.0 equiv) in MeOH (140 mL) was added HCl (4 M in dioxane, 140 mL) dropwise at r.t. The mixture was heated to 80° C. under argon overnight, cooled to r.t., diluted with EA (500 mL), washed with brine (400 mL) three times, dried over anhydrous Na$_2$SO$_4$, concentrated under vacuum, and purified by silica gel column chromatography, eluting with PE/EA (10:1) to afford 12.9 g (80%) of methyl 5-bromo-2,3-dihydro-1H-indene-1-carboxylate as a brown oil.

3. Synthesis of Intermediate 1-4

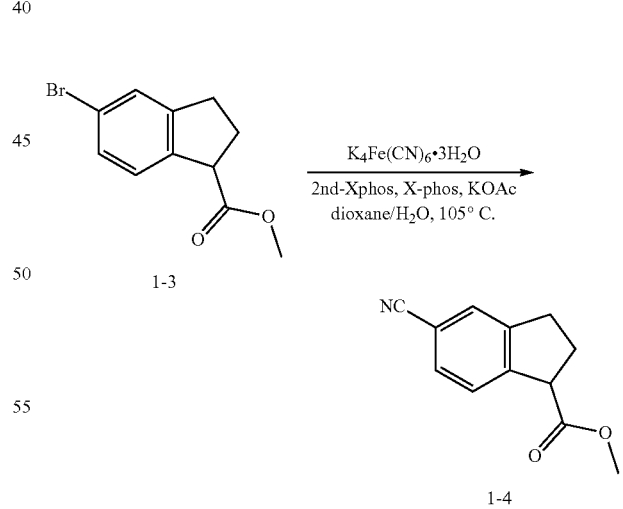

To a stirred solution of methyl 5-bromo-2,3-dihydro-1H-indene-1-carboxylate (12.8 g, 50.3 mmol, 1.0 equiv) in a mixture of 1,4-dioxane/water (50%, 240 mL) under argon atmosphere were added KOAc (9.9 g, 100.5 mmol, 2.0 equiv), K$_4$Fe(CN)$_6$·3H$_2$O (21.2 g, 50.3 mmol, 1.0 equiv), X-phos (1.2 g, 2.51 mmol, 0.05 equiv), and 2nd Generation XPhos precatalyst (2.0 g, 2.51 mmol, 0.05 equiv) at r.t. The mixture was stirred at 105° C. for 2 h, cooled to r.t, diluted with EA (500 mL), washed with brine (400 mL) three times, concentrated under reduced pressure, and then purified by silica gel column chromatography, eluting with PE/EA (20:1), to afford 9.2 g (90%) of methyl 5-cyano-2,3-dihydro-1H-indene-1-carboxylate.

4. Synthesis of Intermediate 1-5

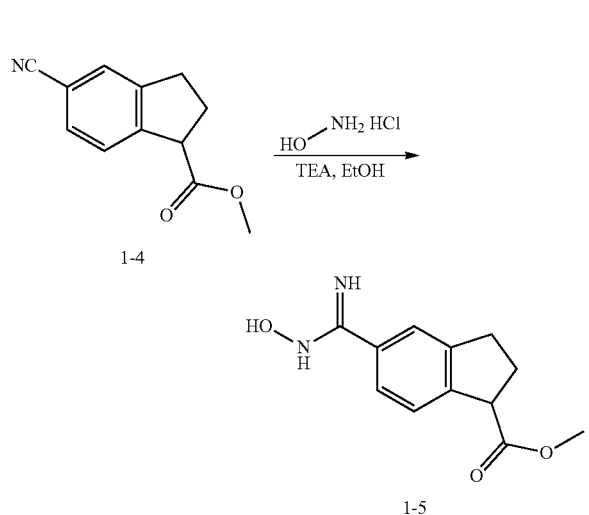

To a stirred solution of methyl 5-cyano-2,3-dihydro-1H-indene-1-carboxylate (1.0 g, 5.0 mmol, 1.0 equiv) in EtOH (10 mL) were added hydroxylamine hydrochloride (518 mg, 7.45 mmol, 1.5 equiv) and TEA (1.5 g, 14.9 mmol, 3.0 equiv) at r.t. The mixture was heated at 65° C. for 2 h and concentrated under vacuum to afford 1.65 g of methyl 5-(N-hydroxycarbamimidoyl)-2,3-dihydro-1H-indene-1-carboxylate as an off-white solid.

5. Synthesis of Intermediate 1-6

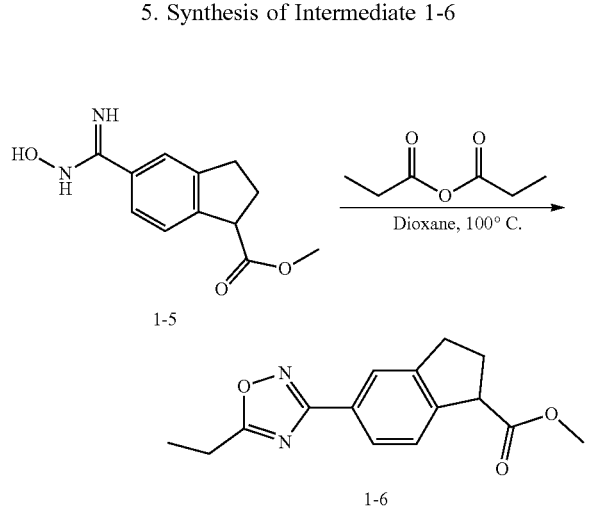

To a stirred solution of methyl 5-(N-hydroxycarbamimidoyl)-2,3-dihydro-1H-indene-1-carboxylate (3 g, 12.8 mmol, 1.0 equiv) in 1,4-dioxane (26 mL) was added propanoyl propanoate (8.3 g, 64.0 mmol, 5.0 equiv) at r.t under argon atmosphere. The mixture was heated at 50° C. for 2 h, then at 100° C. for 2 h, cooled to r.t., diluted with EA (100 mL), washed with brine (150 mL) three times, concentrated under reduced pressure, and purified by silica gel column chromatography, eluting with PE/EA (12:1), to afford 1.65 g (47%) of methyl 5-(5-ethyl-1,2,4-oxadiazol-3-yl)-2,3-dihydro-1H-indene-1-carboxylate as a yellow oil.

6. Synthesis of Intermediate 1-7

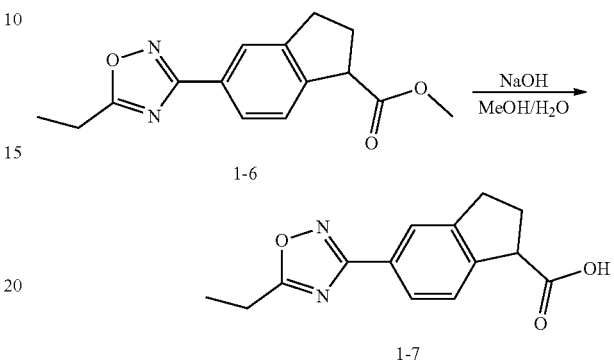

To a stirred solution of methyl 5-(5-ethyl-1,2,4-oxadiazol-3-yl)-2,3-dihydro-1H-indene-1-carboxylate (1.7 g, 6.1 mmol, 1.0 equiv) in MeOH (16 mL) was added sodium hydroxide (836.2 mg, 20.9 mmol, 3.5 equiv) in water (7 mL) dropwise at r.t. The mixture was stirred overnight, acidified to pH 2 with aqueous HCl (2 N), and extracted with DCM (100 mL) four times. The combined organic layers were concentrated under reduced pressure to give 5-(5-ethyl-1,2,4-oxadiazol-3-yl)-2,3-dihydro-1H-indene-1-carboxylic acid as an orange solid. LRMS (ES) 259.

7. Synthesis of Compound 2

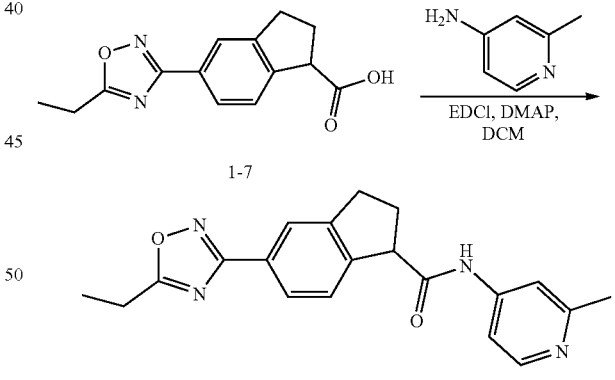

To a stirred solution of 5-(5-ethyl-1,2,4-oxadiazol-3-yl)-2,3-dihydro-1H-indene-1-carboxylic acid (200 mg, 0.8 mmol, 1.0 equiv) in DCM were added EDCI (222 mg, 1.2 mmol, 1.5 equiv), DMAP (142 mg, 1.2 mmol, 1.5 equiv), and 2-methylpyridin-4-amine (126 mg, 1.2 mmol, 1.5 equiv) at r.t. The mixture was stirred overnight, concentrated under reduced pressure, and purified by Prep-HPLC with the following conditions (Column: XBridge Prep C18 OBD Column, 5 μm, 19×150 mm; Mobile Phase A: water (10 mmol/L NH$_4$HCO$_3$), Mobile Phase B: ACN; Flow rate: 20 ml/min; Gradient: 35% B to 48% B in 8 min; 254 nm; RT:

7.43 min) to afford 103 mg (38%) of 5-(5-ethyl-1,2,4-oxadiazol-3-yl)-N-(2-methylpyridin-4-yl)-2,3-dihydro-1H-indene-1-carboxamide as a white solid. LRMS (ES) m/z 349 [M+H]. $^1$H NMR (300 MHz, CD3OD) δ 8.28 (d, J=5.7 Hz, 1H), 8.00-7.84 (m, 2H), 7.62-7.48 (m, 2H), 7.41 (d, J=8.0 Hz, 1H), 4.21 (t, J=7.6 Hz, 1H), 3.29-3.15 (m, 1H), 3.13-2.92 (m, 3H), 2.55-2.41 (m, 5H), 1.43 (t, J=7.6 Hz, 3H).

The following compounds were prepared by methods analogous to the method described for Compound 2:

| Compound No. | LRMS (ES) m/z (M + H) |
|---|---|
| 1 | 338 |
| 5 | 338 |
| 8 | 334 |
| 11 | 286 |
| 14 | 371 |
| 17 | 335 |
| 20 | 361 |
| 23 | 363 |

Example 2

Synthesis of Enantiomers 2A and 2B

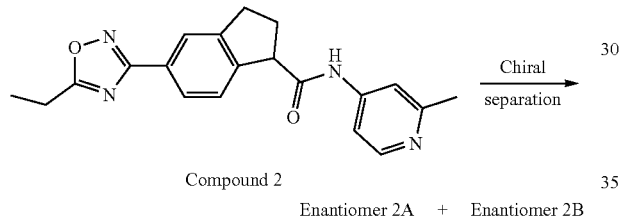

Compound 2 → Enantiomer 2A + Enantiomer 2B

The racemic compound (Compound 2) was separated by preparative Chiral-HPLC with the following conditions (Column: CHIRALPAK IC, 2×25 cm, 5 μm; Mobile Phase A:Hex:DCM=1:1-HPLC, Mobile Phase B: EtOH-HPLC; Flow rate: 18 mL/min; isocratic at 50% B; 220/254 nm, to afford 34 mg of the first eluted peak as Enantiomer 2A and 35 mg of the second eluted peak as Enantiomer 2B. Chiral analytical LC was performed with Conditions A (Conditions A: CHIRALPAK IC-3; 0.46 cm×5 cm; 3 micron; Hex (0.1% DEA):EtOH=50:50 at 1 ml/min flow rate) to give Enantiomer 2A, RT at 1.29 min, and Enantiomer 2B, RT at 3.71 min. Analytical data for Enantiomer 2A: LRMS (ES) m/z 349 (M+H). $^1$H NMR (300 MHz, Methanol-$d_4$) δ 8.29 (d, J=5.8 Hz, 1H), 7.98 (s, 1H), 7.90 (d, J=7.7 Hz, 1H), 7.60 (d, J=2.1 Hz, 1H), 7.53 (dd, J=5.8, 2.1 Hz, 1H), 7.43 (d, J=8.0 Hz, 1H), 4.23 (t, J=7.6 Hz, 1H), 3.24 (dt, J=14.7, 7.0 Hz, 1H), 3.14-2.91 (m, 3H), 2.56-2.42 (m, 5H), 1.44 (t, J=7.6 Hz, 3H). Analytical data for Enantiomer 2B: LRMS (ES) m/z 349[M+H]. $^1$H NMR (300 MHz, Methanol-$d_4$) δ 8.29 (d, J=5.7 Hz, 1H), 7.98 (s, 1H), 7.95-7.85 (m, 1H), 7.60 (d, J=2.1 Hz, 1H), 7.53 (dd, J=5.9, 2.1 Hz, 1H), 7.43 (d, J=7.9 Hz, 1H), 4.23 (t, J=7.6 Hz, 1H), 3.24 (dt, J=14.6, 7.1 Hz, 1H), 3.14-2.91 (m, 3H), 2.56-2.42 (m, 5H), 1.44 (t, J=7.6 Hz, 3H).

The following compounds were separated from the racemic mixture of compounds 5, 8, 11, 14, 17, 20, and 23 by methods analogous to the method described for Compound 2, under the following conditions:

| Enantiomer No. | Chiral Analytical LC Conditions | Retention Time | LRMS (ES) m/z (M + H) |
|---|---|---|---|
| 5A | B | 1.72 | 338 |
| 5B | B | 2.75 | 338 |
| 8A | C | 1.25 | 334 |
| 8B | C | 1.59 | 334 |
| 11A | D | 1.64 | 286 |
| 11B | D | 2.21 | 286 |
| 14A | E | 1.65 | 371 |
| 14B | E | 2.41 | 371 |
| 17A | F | 1.88 | 335 |
| 17B | F | 3 | 335 |
| 20A | A | 1.29 | 361 |
| 20B | A | 3.39 | 361 |
| 23A | A | 1.17 | 363 |
| 23B | A | 3.08 | 363 |

| | Chiral Analytical LC Conditions |
|---|---|
| A | CHIRALPAK IC-3; 0.46 cm × 5 cm; 3 micron; Hex (0.1% DEA):EtOH = 50:50 at 1 ml/min flow |
| B | CHIRALPAK IC-3; 0.46 cm × 5 cm; 3 micron; Hex:EtOH = 50:50 at 1 ml/min flow |
| C | CHIRALPAK IA-3; 0.46 cm × 5 cm; 3 micron; Hex:EtOH = 70:30 at 1 ml/min flow |
| D | CHIRALPAK IG-3; 0.46 cm × 5 cm; 3 micron; Hex (0.1% DEA):IPA = 70:30 at 1 ml/min flow |
| E | CHIRALPAK IG-3; 0.46 cm × 5 cm; 3 micron; Hex (0.1% IPA):EtOH = 50:50 at 1 ml/min flow |
| F | CHIRALPAK IA-3; 0.46 cm × 5 cm; 3 micron; Hex (0.1% DEA):EtOH = 80:20 at 1 ml/min flow |

Example 3

Synthesis of Compound 41

Synthesis of Intermediate 3-2

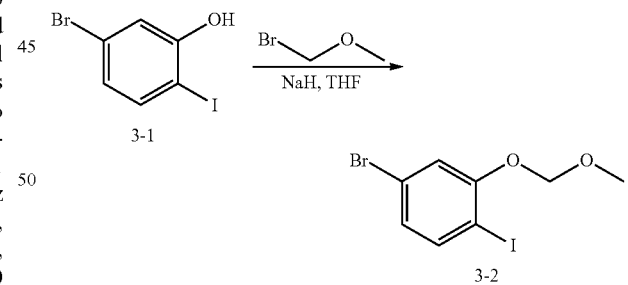

To a stirred solution of 5-bromo-2-iodophenol (9.7 g, 32 mmol, 1.0 equiv) in THF (200 mL) at 0° C. was added NaH (1.69 g, 70 mmol, 2.0 equiv). The mixture was stirred at 0° C. for 15 min and bromo(methoxy)methane (5.25 g, 42.3 mmol, 1.3 equiv) was added dropwise at 0° C. The mixture was stirred for 30 min at 0° C., quenched with water (100 mL), and extracted with EA (150 mL). The organic layer was separated, washed with brine (150 mL) three times, dried over anhydrous sodium sulfate, and concentrated under reduced pressure to give 10.4 g (93%) of 4-bromo-1-iodo-2-(methoxymethoxy)benzene as a yellow oil.

2. Synthesis of Intermediate 3-3

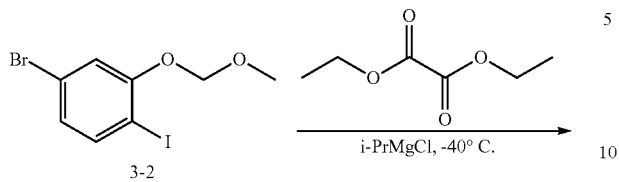

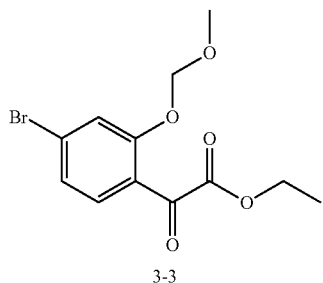

To a stirred solution of 4-bromo-1-iodo-2-(methoxymethoxy)benzene (8.5 g, 24.8 mmol, 1.0 equiv) in THF (85 mL) at −40° C. was added iPrMgCl (2M in THF, 15 mL, 30 mmol, 1.3 equiv) dropwise. The mixture was stirred at −40° C. for 30 min, cooled down to −70° C., followed by the addition of diethyloxalate (5.4 g, 37 mmol, 1.5 equiv). The cold bath was removed. The mixture was stirred at r.t. for 1 h and diluted with aqueous HCl (1 N, 150 mL) and EA (150 mL). The organic layer was separated, washed with brine (200 mL) three times, dried over anhydrous $Na_2SO_4$, concentrated under reduced pressure, and purified by silica gel column chromatography, eluting with EA/PE (1/11) to give 8.5 g of ethyl 2-[4-bromo-2-(methoxymethoxy)phenyl]-2-oxoacetate as an off-white solid.

3. Synthesis of Intermediate 3-4

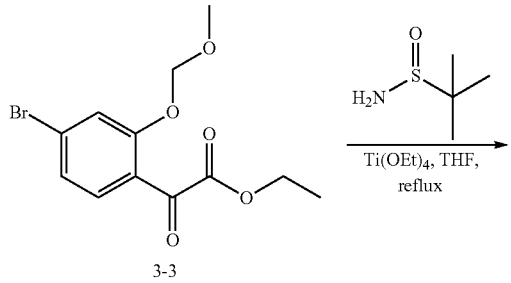

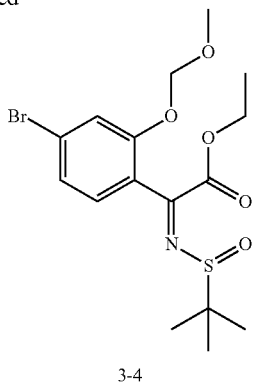

To a stirred solution of ethyl 2-[4-bromo-2-(methoxymethoxy)phenyl]-2-oxoacetate (6.0 g, 18.9 mmol, 1.0 equiv) in THF (60 mL) were added 2-methylpropane-2-sulfinamide (3.0 g, 24.8 mmol, 1.3 equiv) and $Ti(OEt)_4$ (13.0 g, 57.0 mmol, 3.0 equiv) dropwise at r.t. The mixture was heated at 70° C. overnight, cooled to r.t., and poured into a mixture of water and EA (1/1, 200 mL). The organic layer was separated, washed with brine (100 mL) three times, dried over $Na_2SO_4$, and concentrated under reduced pressure to give 3 g (37%) of ethyl (Z)-2-(4-bromo-2-(methoxymethoxy)phenyl)-2-((tert-butylsulfinyl)imino)acetate as a yellow oil.

4. Synthesis of Intermediate 3-5

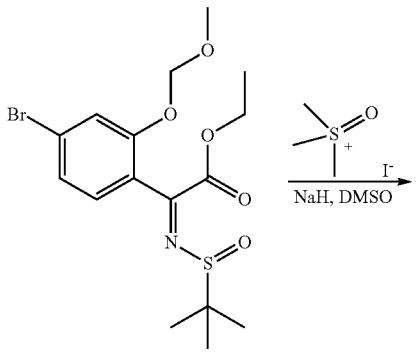

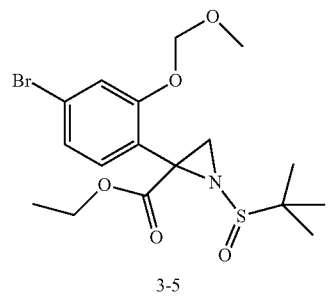

To a stirred solution of trimethylsulfonium iodide (6.6 g, 30 mmol, 3.5 equiv) in DMSO (70 mL) was added NaH (1.03 g, 25.7 mmol, 3.0 equiv) at r.t. The mixture was stirred at r.t. for 1 h, followed by addition of ethyl (Z)-2-(4-bromo-2-(methoxymethoxy)phenyl)-2-((tert-butylsulfinyl)imino) acetate (3.6 g, 8.6 mmol, 1 equiv). The mixture was then heated at 45° C. overnight, cooled to r.t., and diluted with EA (100 mL). The organic layer was separated, washed with brine (150 mL) three times, dried over Na₂SO₄, concentrated under reduced pressure, and purified by silica gel column chromatography, eluting with EA/PE (3/7) to give 4.8 g of ethyl 2-(4-bromo-2-(methoxymethoxy)phenyl)-1-(tert-butylsulfinyl)aziridine-2-carboxylate as a yellow oil.

5. Synthesis of Intermediate 3-6

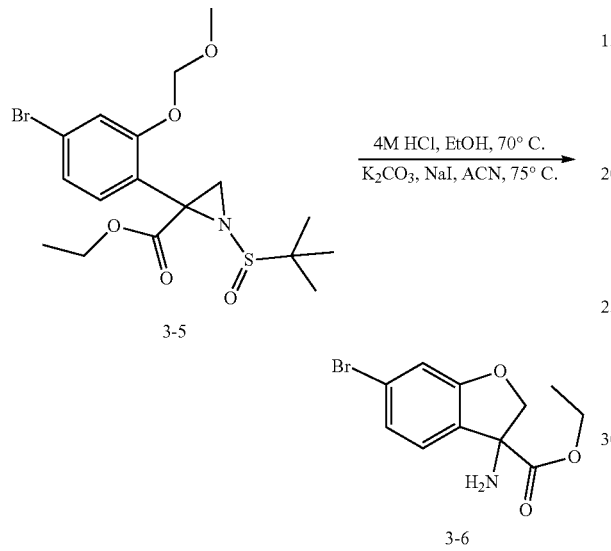

To a stirred solution of ethyl 2-(4-bromo-2-(methoxymethoxy)phenyl)-1-(tert-butylsulfinyl)aziridine-2-carboxylate (4.68 g, 10.77 mmol, 1.0 equiv) in EtOH (80 mL) was added aqueous HCl (4 N, 13 mL, 52 mmol, 5.2 equiv). The mixture was stirred at 70° C. for 3 h and concentrated under reduced pressure. The solid was dissolved in ACN (80 mL), followed by the addition of NaI (320 mg, 2.1 mmol, 0.2 equiv) and K₂CO₃ (3.7 g, 26 mmol, 2.6 equiv) at r.t. The mixture was heated at 75° C. overnight, cooled to r.t., and diluted with EA (80 mL). The organic layer was separated, washed with brine (8 mL) three times, dried over anhydrous sodium sulfate, concentrated under reduced pressure, and purified by C18 silica gel column chromatography, eluting with ACN/water (42%), to give 990 mg (32%) of ethyl 3-amino-6-bromo-2,3-dihydrobenzofuran-3-carboxylate as a yellow oil.

6. Synthesis of Intermediate 3-7

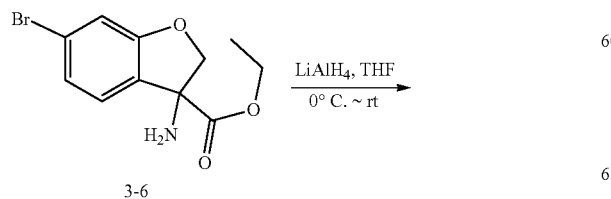

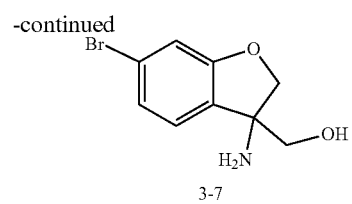

To a stirred solution of ethyl 3-amino-6-bromo-2,3-dihydrobenzofuran-3-carboxylate (930 mg, 3.25 mmol, 1.0 equiv) in THF (15 mL) was added LAH (1 M, 6.5 mL, 6.5 mmol, 2.0 equiv) in portions at 0° C. The mixture was stirred at r.t. for 6 h, cooled back down to 0° C., quenched with water (15 mL), and extracted with EA (20 mL). The organic layer was separated, washed with brine (20 mL) three times, dried over Na₂SO₄, and concentrated under reduced pressure to give 590 mg (74%) of (3-amino-6-bromo-2,3-dihydrobenzofuran-3-yl)methanol as a yellow oil.

7. Synthesis of Intermediate 3-8

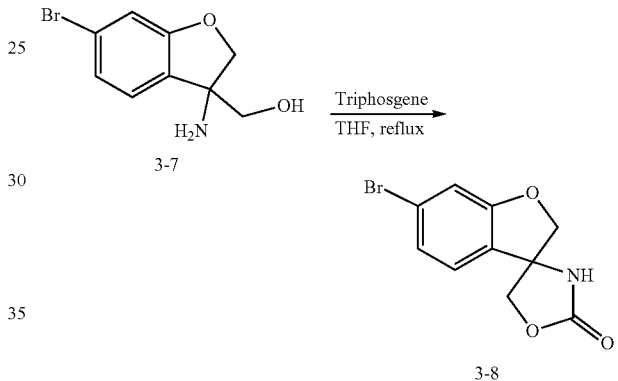

To a stirred solution of (3-amino-6-bromo-2,3-dihydrobenzofuran-3-yl)methanol (570 mg, 2.34 mmol, 1.0 equiv) in THF (6 mL) was added triphosgene (230 mg, 0.78 mmol, 0.33 equiv) at r.t. The mixture was heated at 75° C. overnight and combined with a repeated reaction [393 mg, 1.62 mmol of (3-amino-6-bromo-2,3-dihydro-1-benzofuran-3-yl)methano] together for working up. The combined mixture was diluted with water (10 mL) and filtered to remove the solids. The aqueous layer was extracted with EA (15 ml) three times. The combined organic layers were dried over Na₂SO₄, concentrated under reduced pressure, and purified by C18 silica gel column chromatography, eluting with ACN/water (1/3) to give 660 mg of 6-bromo-2H-spiro[benzofuran-3,4'-oxazolidin]-2'-one as an off-white solid. LRMS (ES) m/z 270/272 (M+H).

8. Synthesis of Intermediate 3-9

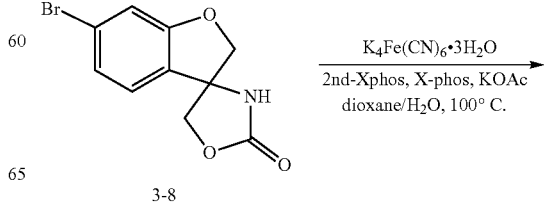

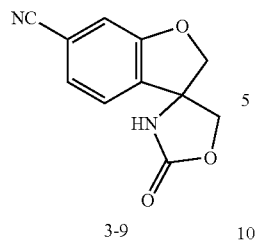

3-9

To a stirred solution of 6-bromo-2H-spiro[benzofuran-3,4'-oxazolidin]-2'-one (305 mg, 1.13 mmol, 1.0 equiv) in a mixture of dioxane/water (1/1, 6 mL) were added K₄Fe(CN)₆·3H₂O (478 mg, 1.13 mmol, 1.0 equiv), X-phos (108 mg, 0.23 mmol, 0.2 equiv), 2nd Generation XPhos precatalyst (178 mg, 0.23 mmol, 0.2 equiv) and KOAc (333 mg, 3.39 mmol, 3.0 equiv) at r.t. The mixture was stirred at 100° C. overnight, cooled to r.t., filtered to remove solids, and extracted with EA (100 mL) three times. The combined organic layers were dried over Na₂SO₄, concentrated under reduced pressure, and purified by C18 silica gel column chromatography, eluting with ACN/water (21%) to give 180 mg (73%) of 2'-oxo-2H-spiro[benzofuran-3,4'-oxazolidine]-6-carbonitrile as a white solid. LRMS (ES) m/z 217 (M+H).

9. Synthesis of Intermediate 3-10

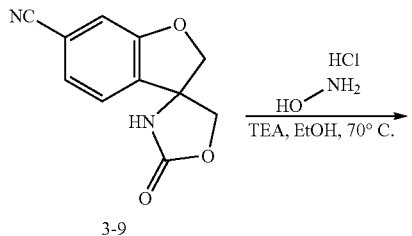

3-9

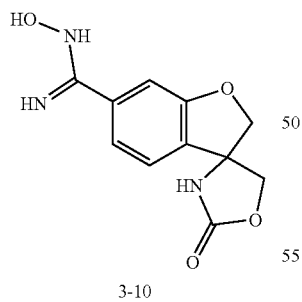

3-10

To a stirred solution of 2'-oxo-2H-spiro[benzofuran-3,4'-oxazolidine]-6-carbonitrile (148 mg, 0.68 mmol, 1.0 equiv) in EtOH (3 mL) were added TEA (173 mg, 1.71 mmol, 2.5 equiv) and hydroxylamine hydrochloride (95 mg, 1.36 mmol, 2.0 equiv) at r.t. The mixture was heated at 50° C. overnight and concentrated under reduced pressure to give 286 mg of N-hydroxy-2'-oxo-2H-spiro[benzofuran-3,4'-oxazolidine]-6-carboximidamide as a white solid. LRMS (ES) m/z 250 (M+H).

10. Synthesis of Compound 41

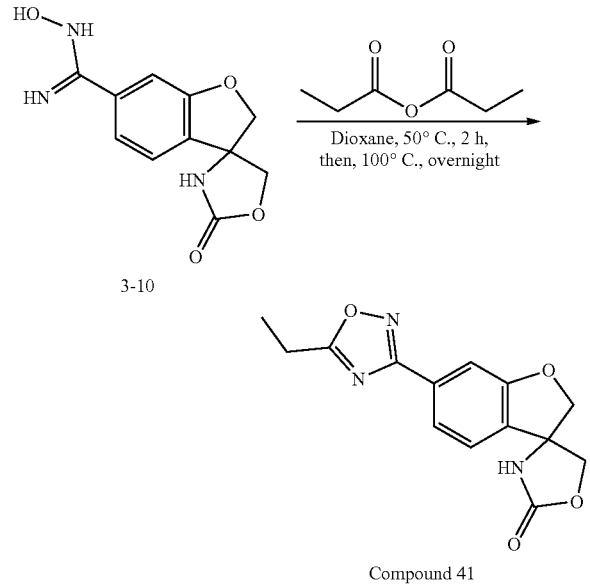

Compound 41

To a stirred solution of N-hydroxy-2'-oxo-2H-spiro[benzofuran-3,4'-oxazolidine]-6-carboximidamide (286 mg, 1.15 mmol, 1.0 equiv) in dioxane (6 mL) was added propanoyl propanoate (448 mg, 3.44 mmol, 3.0 equiv) at r.t. The mixture was stirred at 50° C. for 2 h and at 100° C. overnight, cooled to r.t., concentrated, and purified by Prep-HPLC with the following conditions (Column: XBridge Prep OBD C18 Column 150 mm×5 μm; Mobile Phase A: water (10 mmol/L NH₄HCO₃), Mobile Phase B: ACN; Flow rate: 60 mL/min; Gradient: 25% B to 36% B in 8 mM; 254 nm; RT: 7.92 min) to give 86 mg (26%) of 6-(5-ethyl-1,2,4-oxadiazol-3-yl)-2H-spiro[benzofuran-3,4'-oxazolidin]-2'-one as a white solid. LRMS (ES) m/z 288 (M+H). ¹H NMR (400 MHz, Chloroform-d) δ 7.80 (dd, J=8.0, 1.3 Hz, 1H), 7.60 (s, 1H), 7.51 (d, J=7.9 Hz, 1H), 5.51 (s, 1H), 4.71-4.55 (m, 4H), 3.01 (q, J=7.6 Hz, 2H), 1.58 (s, 1H), 1.52 (d, J=17.7 Hz, 1H), 1.46 (s, 1H).

Example 4

Synthesis of Enantiomers 41A and 41B

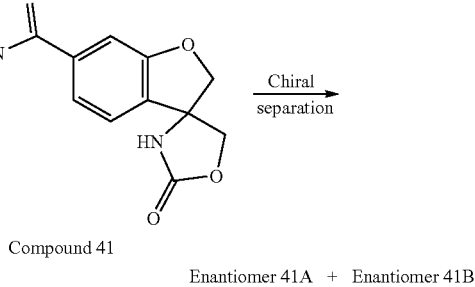

Compound 41

Enantiomer 41A + Enantiomer 41B

The racemic compound (Compound 41) was separated by chiral-HPLC with the following conditions (Column: CHI- RALPAK IE, 2×25 cm, 5 μm; Mobile Phase A:Hex: DCM=3:1 (10 mM $NH_3$-MeOH), Mobile Phase B: EtOH; Flow rate: 15 mL/min; Gradient: 50 B to 50 B in 15 min; 220/254 nm) to give two peaks. The first eluted peak is assigned as Enantiomer 41A (10 mg) and the second eluted peak is assigned as Enantiomer 41B (20 mg). Chiral analytical LC was performed with Conditions G (Conditions G: CHIRALPAK IE-3; 0.46 cm×5 cm; 3 micron; Hex (0.1% DEA):EtOH=50:50 at 1 mL/min flow) to give Enantiomer 41A, RT at 2.65 min and Enantiomer B RT at 4.35 min. Analytical data for Enantiomer 41A: LRMS (ES) m/z 288 (M+H). $^1$H NMR (300 MHz, Methanol-d4) δ 7.74 (dd, J=7.9, 1.4 Hz, 1H), 7.57 (d, J=7.9 Hz, 1H), 7.49 (d, J=1.4 Hz, 1H), 4.72-4.58 (m, 4H), 3.00 (q, J=7.6 Hz, 2H), 1.43 (t, J=7.6 Hz, 3H). Analytical data for Enantiomer 41B: LRMS (ES) m/z 288 (M+H). $^1$H NMR (300 MHz, Methanol-d4) δ 7.74 (dd, J=7.9, 1.4 Hz, 1H), 7.57 (d, J=7.9 Hz, 1H), 7.49 (d, J=1.4 Hz, 1H), 4.72-4.58 (m, 4H), 3.00 (q, J=7.6 Hz, 2H), 1.43 (t, J=7.6 Hz, 3H).

Example 5

Synthesis of Compound 26

1. Synthesis of Intermediate 5-2

To a solution of 5-bromo-2,3-dihydro-1H-inden-1-one (10 g, 47.4 mmol, 1.0 equiv) in a mixture of DMF (105 mL) and water (55 mL) was added ammonium carbonate (20.5 g, 213 mmol, 4.5 equiv) at r.t. The mixture was stirred at r.t for 30 min, followed by the addition of sodium carbonitrile (3.5 g, 71.1 mmol, 1.5 equiv), heated at 50° C. for 58 h, cool down to r.t, quenched with water (500 mL), and extracted with EA (500 mL) twice. The combined organic layers were washed with water (500 mL) twice, dried over anhydrous sodium sulfate, and concentrated under reduced pressure to give 7.7 g (57.8%) of 5'-bromo-2',3'-dihydrospiro[imidazolidine-4,1'-indene]-2,5-dione as a white solid.

2. Synthesis of Intermediate 5-3

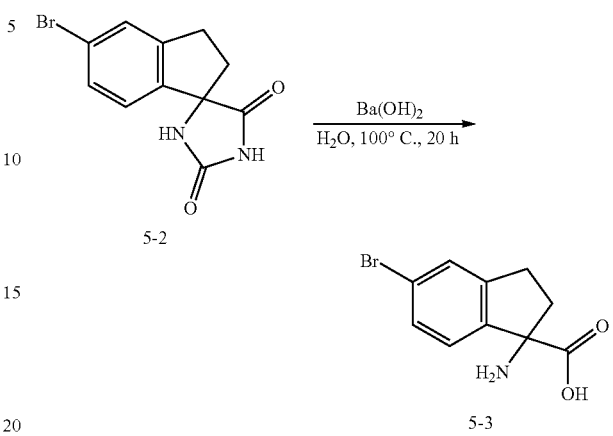

To a solution of 5'-bromo-2',3'-dihydrospiro[imidazolidine-4,1'-indene]-2,5-dione (3.0 g, 10 mmol, 1.0 equiv) in water (30 mL) was added $Ba(OH)_2·8H_2O$ (4.6 g, 26.9 mol, 2.5 equiv) at r.t. The mixture was stirred at 100° C. for 15 h, cooled to r.t, adjusted the pH to 1.5 by adding aqueous H2504 (1 M) dropwise. The solid was filtered and filtrate was concentrated under vacuum to give 2.4 g (88%) of 1-amino-5-bromo-2,3-dihydro-1H-indene-1-carboxylic acid.

3. Synthesis of Intermediate 5-4

To a stirred solution of 1-amino-5-bromo-2, 3-dihydro-1H-indene-1-carboxylic acid (1.14 g, 4.45 mmol, 1.0 equiv) in THF (16 mL) was added $BH_3$-$Me_2S$ (3.8 mL, 50.0 mmol, 9.0 equiv) at r.t. The mixture was stirred at 75° C. for 3 days, cooled to 0° C., followed by the addition of MeOH (5 mL), concentration under reduced pressure, and purification by C18 silica gel column chromatography eluting with ACN/$H_2O$ (50%) to afford 231 mg (21%) of (1-amino-5-bromo-2,3-dihydro-1H-inden-1-yl)methanol as a white solid.

4. Synthesis of Intermediate 5-5

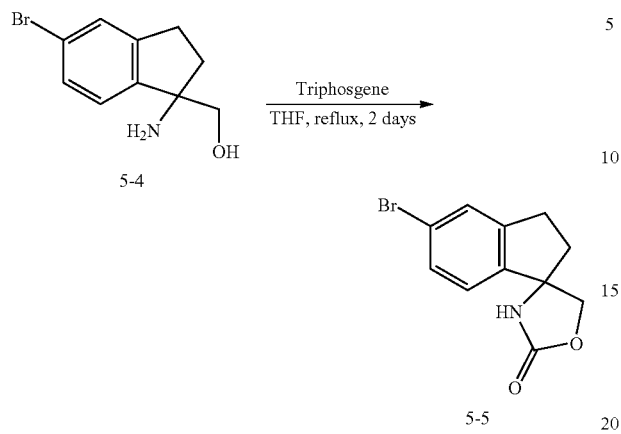

To a solution of (1-amino-5-bromo-2, 3-dihydro-1H-inden-1-yl) methanol (1.0 g, 4.1 mol, 1.0 equiv) in THF (10 mL) was added triphosgene (0.6 g, 2.0 mol, 0.5 equiv) at r.t. The mixture was heated at 70° C. for 10 h, cooled to 0° C., quenched with MeOH (2 mL), concentration under reduced pressure, and purification by silica gel column chromatography, eluting with EA and PE (1/1) to afford 600 mg (54%) of 5-bromo-2,3-dihydrospiro[indene-1,4'-oxazolidin]-2'-one as a white solid.

5. Synthesis of Intermediate 5-6

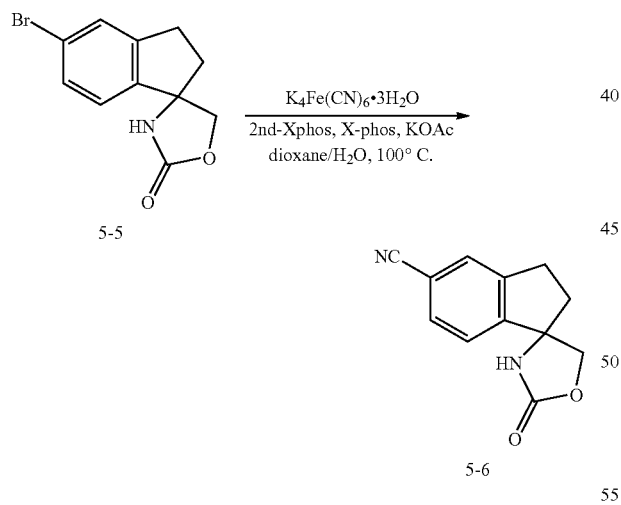

To a solution of 5-bromo-2,3-dihydrospiro[indene-1,4'-oxazolidin]-2'-one (500 mg, 1.86 mol, 1.0 equiv) in a mixture of dioxane and water (1/1, 5 mL) were added potassium acetate (366 mg, 3.73 mol, 2.0 equiv), K₄Fe(CN)₆·3H₂O (315 mg, 0.4 equiv), 2nd generation Xphos precatalyst (22 mg, 0.015 equiv), and X-phos (13 mg, 0.015 equiv) at r.t. The mixture was stirred at 100° C. for 4 h, cooled to r.t, and extracted with EtOAc (10 mL) twice. The combined organic layers were washed with brine (20 mL), dried over anhydrous Na₂SO₄, concentrated under reduced pressure, and purified by Prep-TLC (PE/EtOAc 1:1) to afford 340 mg (85%) of 2'-oxo-2,3-dihydrospiro[indene-1,4'-oxazolidine]-5-carbonitrile as a white solid.

6. Synthesis of Intermediate 5-7

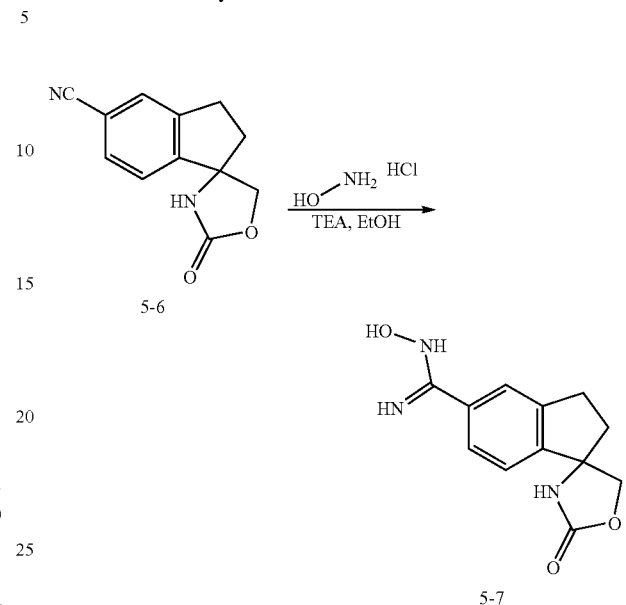

To a solution of 2'-oxo-2,3-dihydrospiro[indene-1,4'-oxazolidine]-5-carbonitrile (350 mg, 1.63 mol, 1.0 equiv) in EtOH (5 mL) were added TEA (47 mg, 0.47 mmol, 2.0 equiv) and hydroxylamine hydrochloride (227 mg, 3.26 mol, 2.0 equiv) at r.t. The mixture was stirred overnight at r.t., concentrated under reduced pressure, diluted with water (30 mL), and extracted with EtOAc (25 mL) three times. The combined organic layers were washed with brine (100 mL), dried over anhydrous Na$_2$SO$_4$, and concentrated under reduced pressure to give 305 mg (76%) of N-hydroxy-2'-oxo-2,3-dihydrospiro[indene-1,4'-oxazolidine]-5-carboximidamide as a light yellow solid.

7. Synthesis of Compound 26

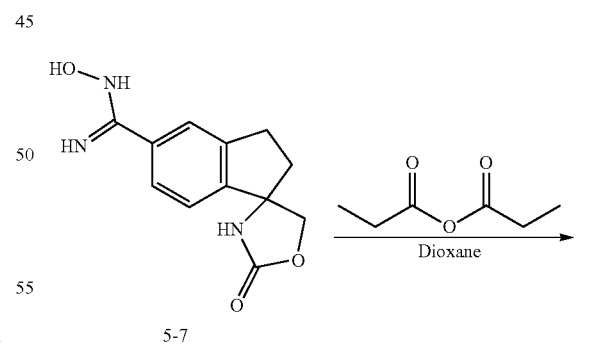

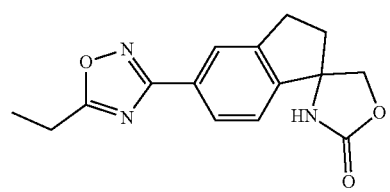

Compound 26

To a solution of N'-hydroxy-2'-oxo-2,3-dihydrospiro[indene-1,4'-oxazolidine]-5-carboximidamide (80 mg, 320 mmol, 1.0 equiv) in dioxane (1 mL) was added propanoyl propanoate (42 mg, 320 mmol, 1.0 equiv) at r.t. The mixture was heated at 50° C. for 1 h and at 100° C. for 4 h, cooled to r.t, concentrated under reduced pressure, and purified by C18 silica gel column chromatography with the following conditions (Phase A: Water (10 mmol/L NH$_4$HCO$_3$) Phase B: ACN) to afford 7 mg (8%) of 5-(5-ethyl-1,2,4-oxadiazol-3-yl)-2,3-dihydrospiro[indene-1,4'-oxazolidin]-2'-one as a white solid. LRMS (ES) m/z 286 [M+H]. $^1$HNMR: (300 MHz, Chloroform-d, ppm) δ 8.12-7.96 (m, 2H), 7.55 (d, J=8.0 Hz, 1H), 5.27 (s, 1H), 4.50 (d, J=8.7 Hz, 1H), 4.40 (d, J=8.7 Hz, 1H), 3.12-2.91 (m, 4H), 2.65-2.51 (m, 1H), 2.36 (dt, J=13.6, 8.7 Hz, 1H), 1.49 (t, J=7.6 Hz, 3H).

The following compound was prepared by methods analogous to the method described for Compound 26:

| Compound No. | LRMS (ES) m/z (M + H) |
|---|---|
| 29 | 272 |
| 32 | 300 |
| 35 | 298 |
| 38 | 308 |

Example 6

Synthesis of Enantiomers 26A and 26B

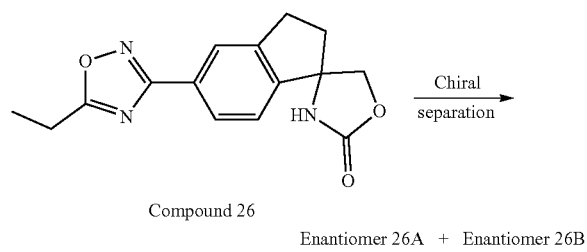

Compound 26 → Enantiomer 26A + Enantiomer 26B (Chiral separation)

The racemic compound 5-(5-ethyl-1,2,4-oxadiazol-3-yl)-2,3-dihydrospiro[indene-1,3-[1,4]oxazolidine]-5-one (70 mg, 0.25 mmol, 1 equiv) (Compound 26) was separated by Chiral-HPLC with the follow conditions (Column: Chiralpak IA, 2×25 cm, 5 µm; Mobile Phase A: Hex, Mobile Phase B: EtOH; Flow rate: 15 mL/min; Gradient: 50 B to 50 B in 18 min; 254/220 nm) to give two peaks. The first eluted peak is assigned as Enantiomer 26A (31 mg) and the second eluted peak is assigned as Enantiomer 26B (32 mg). Chiral analytical LC was performed with Conditions H (Conditions H: CHIRAL Cellulose-SB; 0.46 cm×15 cm; 5 micron; Hex (0.1% DEA):EtOH=70:30 at 1 mL/min flow rate) to give Enantiomer 26A, RT at 5.28 min, and Enantiomer 26B, RT at 5.93 min. Analytical data for Enantiomer 26A: LRMS (ES) m/z 286 (M+H). $^1$H NMR (400 MHz, Chloroform-d, ppm) δ 8.07 (d, J=7.8 Hz, 1H), 7.99 (s, 1H), 7.54 (d, J=8.0 Hz, 1H), 5.16 (br, 1H), 4.50 (d, J=8.7 Hz, 1H), 4.40 (d, J=8.8 Hz, 1H), 3.12-2.91 (mm, 4H), 2.62-2.50 (m, 1H), 2.42-2.29 (m, 1H), 1.49 (t, J=7.6 Hz, 3H). Analytical data for Enantiomer 26B: LRMS (ES) m/z 286 (M+H). $^1$H NMR (400 MHz, Chloroform-d) δ 8.06 (d, J=8.0 Hz, 1H), 7.99 (s, 1H), 7.54 (d, J=8.0 Hz, 1H), 5.21 (s, 1H), 4.50 (d, J=8.7 Hz, 1H), 4.40 (d, J=8.7 Hz, 1H), 3.13-2.94 (m, 4H), 2.63-2.52 (m, 1H), 2.39-2.28 (m, 1H), 1.49 (t, J=7.6 Hz, 3H).

The following compounds were separated from the racemic mixture of compounds 29, 32, 35, and 38 by methods analogous to the method described for Compound 26, under the following conditions:

| Enantiomer No. | Chiral Analytical LC Conditions | Retention Time | LRMS (ES) m/z (M + H) |
|---|---|---|---|
| 29A | I | 6.7 | 272 |
| 29B | I | 7.6 | 272 |
| 32A | J | 2.38 | 300 |
| 32B | J | 2.97 | 300 |
| 35A | K | 3.13 | 298 |
| 35B | K | 3.62 | 298 |
| 38A | L | 2.22 | 308 |
| 38B | L | 2.67 | 308 |

Chiral Analytical LC Conditions

| | | |
|---|---|---|
| H | CHIRAL Cellulose-SB; 0.46 cm × 15 cm; 5 micron; Hex (0.1% DEA):EtOH = 70:30 at 1 ml/min flow rate | |
| I | CHIRAL Cellulose-SB; 0.46 cm × 10 cm; 3 micron; Hex (0.1% DEA):EtOH = 80:20 at 1 ml/min flow rate | |
| J | CHIRALPAK IC-3; 0.46 cm × 5 cm; 3 micron; Hex (20 mM NH$_3$):EtOH = 50:50 at 1 ml/min flow rate | |
| K | CHIRALPAK Cellulose-SB; 0.46 cm × 15 cm; 3 micron; MtBE (0.1% DEA):EtOH = 80:20 at 1 ml/min flow rate | |
| L | CHIRALPAK IC-3; 0.46 cm × 5 cm; 3 micron; (Hex:DCM = 3:1)(0.1% DEA):EtOH = 85:15 at 1 ml/min flow rate | |

Biological Example B-1

Myofibril Assays

To evaluate the effect of compounds on the ATPase activity of full-length cardiac myosin in the context of the native sarcomere, skinned myofibril assays were performed. Bovine cardiac myofibrils were obtained by homogenizing bovine cardiac left ventricular tissue in the presence of a detergent such as triton X-100. Such treatment removes membranes and a majority of the soluble cytoplasmic proteins but leaves intact the cardiac sarcomeric acto-myosin apparatus. Myofibril preparations retain the ability to hydrolyze ATP in an Ca$^{2+}$ regulated manner ATPase activities of such myofibril preparations in the presence and absence of compounds were assayed at Ca$^{2+}$ concentrations activating to a defined fraction of the maximal rate (i.e., 25%, 75%). Small molecule agents were assessed for their ability to inhibit the steady-state ATPase activity of bovine cardiac myofibrils using pyruvate kinase and lactate dehydrogenase (PK/LDH)-coupled enzyme system. This assay regenerates myosin-produced ADP into ATP by oxidizing NADH, producing an absorbance change at 340 nm. Prior to testing small molecule agents, the bovine cardiac myofibrils were assessed for their calcium responsiveness and the calcium concentration that achieves either a 50% (pCa$_{50}$) or 75% (pCa$_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM 12 buffer). Final assay conditions were 1 mg/mL of bovine cardiac myofibrils, 4 U/mL pyruvate kinase, 6 U/mL lactate dehydrogenase, 50 µM ATP, 0.1 mg/mL BSA (bovine serum albumin), 10 ppm antifoam, 1 mM DTT, 0.5 mM NADH, 1.5 mM PEP, 0.6 mM EGTA, and an amount of $CaCl_2$) sufficient to achieve either 50% or 75% activation of the myofibril ATPase activity. Results for compounds tested are provided in Table A. Compounds tested were prepared in accordance with the synthetic procedures described herein.

TABLE A

| Cmpd No. | Enantiomer No. | CDMF75 $IC_{15}$ (µM) | CDMF75 $IC_{50}$ (µM) |
|---|---|---|---|
| 1 | — | 3.9 | 15.9 |
| 2 | — | 1.6 | 5.5 |
| — | 2A | 0.7 | 3.0 |
| — | 2B | 17.5 | >39.2 |
| 5 | — | >39.2 | >39.2 |
| — | 5A | >39.2 | >39.2 |
| — | 5B | >39.2 | >39.2 |
| 8 | — | 1.3 | 6.1 |
| — | 8A | 0.7 | 2.8 |
| — | 8B | >39.2 | >39.2 |
| 11 | — | >39.2 | >39.2 |
| — | 11A | >39.2 | >39.2 |
| — | 11B | 26.3 | >39.2 |
| 14 | — | 4.4 | 23.1 |
| — | 14A | 2.2 | 11 |
| — | 14B | >39.2 | >39.2 |
| 17 | — | 6.0 | 33.4 |
| — | 17A | 2.9 | 13.6 |
| — | 17B | >39.2 | >39.2 |
| 20 | — | 2.6 | 13.9 |
| — | 20A | 1.2 | 5.6 |
| — | 20B | 33.2 | >39.2 |
| 23 | — | 5.6 | 29.0 |
| — | 23A | 3.6 | 14.6 |
| — | 23B | >39.2 | >39.2 |
| 26 | — | 0.8 | 3.0 |
| — | 26A | 31.0 | >39.2 |
| — | 26B | 0.3 | 1.6 |
| 29 | — | 4.2 | 18.4 |
| — | 29A | >39.2 | >39.2 |
| — | 29B | 2.1 | 9.1 |
| 32 | — | 2.7 | 11.4 |
| — | 32A | 1.5 | 6.3 |
| — | 32B | >39.2 | >39.2 |
| 35 | — | 1.5 | 5.8 |
| — | 35A | >39.2 | >39.2 |
| — | 35B | 0.6 | 3.4 |
| 38 | — | 2.5 | 14.1 |
| — | 38A | 1.8 | 7.5 |
| — | 38B | >39.2 | >39.2 |
| 41 | — | 0.6 | 2.2 |
| — | 41A | 0.2 | 1.0 |
| — | 41B | >39.2 | >39.2 |

Biological Example B-2

Myocyte Assays (i) Preparation of Adult Cardiac Ventricular Rat Myocytes

Adult male Sprague-Dawley rats are anesthetized and the hearts are quickly excised, rinsed and the ascending aorta is cannulated. Continuous retrograde perfusion is initiated on the hearts at a perfusion pressure of 60 cm H2O. Hearts are first perfused with a nominally $Ca^{2+}$-free modified Krebs solution of the following composition: 113 mM NaCl, 4.7 mM KCl, 0.6 mM $KH_2PO_4$, 0.6 mM $Na_2HPO_4$, 1.2 mM $MgSO_4$, 12 mM $NaHCO_3$, 10 mM $KHCO_3$, 30 mM taurine, 5.5 mM glucose and 10 mM Hepes (all Sigma). This medium is not recirculated and is continually aerated with a 95% $O_2$/5% $CO_2$ mixture. After approximately 3 minutes the heart is perfused with a modified Krebs buffer supplemented with collagenase (Worthington) and 12.5 µM final calcium concentration. The heart is removed from the cannulae after the heart appears blanched and soft in appearance. The atria and vessels are removed and the ventricles are gently dissected into smaller pieces with forceps. The tissue is homogenized by repeated pipette trituration and the collagenase reaction is stopped by 10% bovine calf serum (BCS), sedimentation and resuspension in perfusion buffer containing 5% BCS and 12.5 uM $CaCl_2$). Myocytes are made calcium tolerant by stepwise addition of a $CaCl_2$) solution to a final concentration of 1.2 mM. Cells are then washed and resuspended in Tyrode's buffer (137 mM NaCl, 3.7 mM KCl, 0.5 mM MgCl, 11 mM glucose, 4 mM Hepes, and 1.2 mM $CaCl_2$, pH 7.4). Cells are kept for 60 min at 37° C. prior to initiating experiments and used within 5 hrs of isolation. Preparations of cells are used only if cells first passed QC criteria by demonstrating a contractile response to standard (>150% of basal) and isoproterenol (ISO; >250% of basal) treatment. Additionally, only cells whose basal contractility is between 3 and 8% are used in subsequent experiments with compounds.

(II) Adult Ventricular Myocyte Contractility Experiments

Aliquots of myocytes in Tyrode's buffer are placed in perfusion chambers (series 20 RC-27NE; Warner Instruments) complete with heating platforms. Myocytes are allowed to attach, the chambers are heated to 37° C., and the cells are perfused with 37° C. Tyrode's buffer. Myocytes are field stimulated at 1 Hz in with platinum electrodes (20% above threshold). Only cells that have clear striations and are quiescent prior to pacing are used for contractility experiments. To determine basal contractility, myocytes are imaged through a 40× objective. Using a variable frame rate (60-240 Hz) charge-coupled device camera, the images are digitized and displayed on a computer screen at a sampling speed of 240 Hz (IonOptix Milton, Mass.). Once cell contraction is stable over time, test compounds (0.01-15 µM) are perfused into the chambers on the myocytes for 5 minutes. Contractility of the myocytes and contraction and relaxation velocities is then recorded using edge detection.

(III) Contractility Analysis

Five or more individual myocytes are tested per compound from two or more different myocyte preparations. For each cell, twenty or more contractility transients at basal (defined as 1 min prior to compound infusion) and after compound addition (defined as 5 min after starting compound perfusion), are averaged and compared. These average transients are analyzed using the IonWizard software (IonOptix) to determine changes in diastolic length and fractional shortening. Fractional shortening is calculated as: ((resting length−length at peak contraction) divided by the resting length). The percent change in fractional shortening from baseline is calculated as: ((post-dose fractional shortening/basal fractional shortening)*100). The percent reduction in fractional shortening from baseline is calculated as: (100−percent change in fractional shortening from baseline). Maximum contraction and relaxation velocities (um/sec) is also determined. Results from individual cells are averaged and the SEM is calculated.

Biological Example B-3

Echocardiography assessment of acute pharmacodynamic effect in rat cardiac contractility.

Assessment of in vivo cardiac function by echocardiography is performed in male Sprague Dawley rats under isoflurane (1-3%) anesthesia. 2-D M-mode images of the left ventricle are acquired in the parasternal long-axis view before, during, and after administration of compounds by continuous IV infusion or oral gavage. In vivo fractional shortening is determined by M-mode image analysis with the following calculation: ((End diastolic diameter–end systolic diameter)/end diastolic diameter×100). For continuous IV infusion experiments, three pre-dose baseline M-mode images are taken at 1 minute intervals prior to infusion of compound. Compounds are formulated in 50% Propylene Glycol (PG): 16% Captisol: 10% dimethylacetamide (DMA) and delivered via a jugular vein catheter at the rate of 1 mL/kg/h. During infusion, M-mode images are taken at 5 minute intervals. The infusion is stopped when fractional shortening reaches up to a 60% reduction from baseline. Blood samples are taken to determine the plasma concentration of the compounds. Data may be reported as an estimated $IC_{50}$ value, which is the concentration at which fractional shortening is 50% of the pre-dose baseline contractility.

For oral dosing studies, three pre-dose baseline M-Mode images are taken at 1 minute intervals prior to compound administration. Compounds are formulated in a 0.5% hydroxypropyl methylcellulose 2910 (HPMC 2910): 0.1% Tween 80 suspension and delivered as a single dose (5 mL/kg) by oral gavage. At one and four hours post-dose, rats are lightly anesthetized for M-mode echocardiography measurement. The compound effect on cardiac fractional shortening may be presented as a percent reduction of baseline fractional shortening (=100%)

Concurrent with echocardiography measurements, blood samples are taken to determine the corresponding compound plasma concentration, which may be represented as $IC_{50}$ and $IC_{10}$ values, which is the concentration at which fractional shortening is 50% and 10% of the pre-dose baseline contractility, respectively.

Biological Example B-4

Longitudinal Echocardiography Assessment of Mouse Model of HCM

Assessment over time of in vivo cardiac function by echocardiography is performed using a previously reported mouse model of familial hypertrophic cardiomyopathy, which is generated by an arginine to glutamine mutation at residue 403 (R403Q) of the alpha cardiac myosin heavy chain (MHC) gene (Geisterfer-Lowrance et al., Science. 1996 May 3; 272(5262):731-4). Cardiac dysfunction, fibrosis, and measures of cardiac hypertrophy (including ventricular wall thickness) increase with age in this mouse model (Geisterfer-Lowrance, supra; Jiang et al., Science. 2013, 342(6154):111-4).

R403Q mice receive vehicle or test compound formulated in chow for 24 weeks. Longitudinal echocardiography measurements are performed every 4 weeks. Echocardiography measurements are taken with mice under isoflurane (1-3%) anesthesia. 2-D M-mode images of the left ventricle are acquired in short-axis view. In vivo fractional shortening is determined by M-Mode image analysis with the following calculation: ((End diastolic diameter–end systolic diameter)/end diastolic diameter×100).

Biological Example B-5

Fibrosis Reduction in a Rat Model of Cardiac Hypertrophy

Assessment of fibrosis reduction is performed using Dahl Salt Sensitive (DSS) rats, a previously reported hypertension-induced rat model of heart failure with preserved ejection fraction (Fillmore et al., Mol Med. 2018, 24(1):3; Dahl et al., J Exp Med. 1962, 115:1173-90). DSS rats fed a high salt diet demonstrate progressive cardiovascular dysfunction, including increased systolic blood pressure, diastolic dysfunction, cardiac hypertrophy, and cardiac fibrosis (Fillmore, supra; Dahl, supra, Sakata et al., J Am Coll Cardiol. 2001 January; 37(1):293-9; Kim-Mitsuyama et al., Hypertens Res. 2004 October; 27(10):771-9).

DSS rats receive vehicle or test compound formulated in low or high salt chow for 6 weeks. Perivascular and interstitial cardiac tissue samples are imaged and assayed for % cardiac fibrosis.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:
1. A compound of Formula (I):

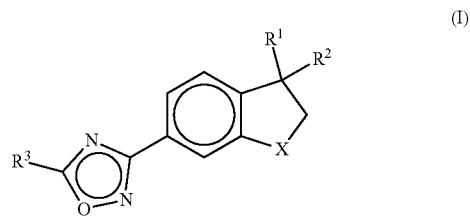

or a pharmaceutically acceptable salt thereof, wherein:
X is —O— or —$CH_2$—;
$R^1$ and $R^2$ taken together are —$CH_2$OC(O)NH—; and
$R^3$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocyclyl, substituted or unsubstituted aryl, and substituted or unsubstituted heteroaryl.

2. The compound of claim 1, or a pharmaceutically acceptable salt thereof, wherein X is —$CH_2$—.

3. The compound of claim 1, or a pharmaceutically acceptable salt thereof, wherein X is —O—.

4. The compound of claim 1, or a pharmaceutically acceptable salt thereof, wherein $R^3$ is substituted or unsubstituted alkyl, or substituted or unsubstituted cycloalkyl.

5. The compound of claim 1, or a pharmaceutically acceptable salt thereof, wherein $R^3$ is methyl, ethyl, propyl, isopropyl, or butyl.

6. The compound of claim 1, or a pharmaceutically acceptable salt thereof, wherein $R^3$ is haloalkyl.

7. The compound of claim 1, or a pharmaceutically acceptable salt thereof, wherein $R^3$ is —$CHF_2$.

8. The compound of claim 1, or a pharmaceutically acceptable salt thereof, wherein $R^3$ is cyclopropyl.

9. A compound selected from the group consisting of

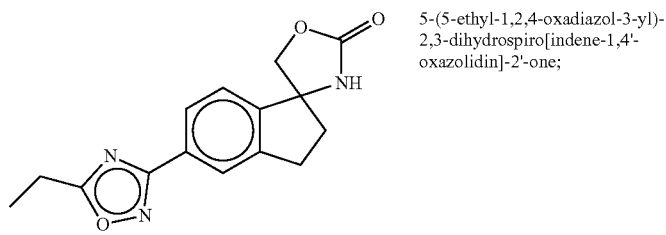

5-(5-ethyl-1,2,4-oxadiazol-3-yl)-2,3-dihydrospiro[indene-1,4'-oxazolidin]-2'-one;

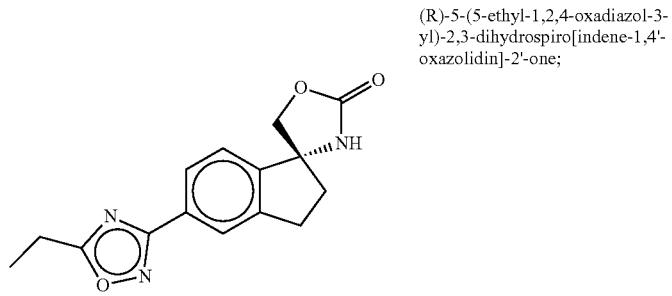

(R)-5-(5-ethyl-1,2,4-oxadiazol-3-yl)-2,3-dihydrospiro[indene-1,4'-oxazolidin]-2'-one;

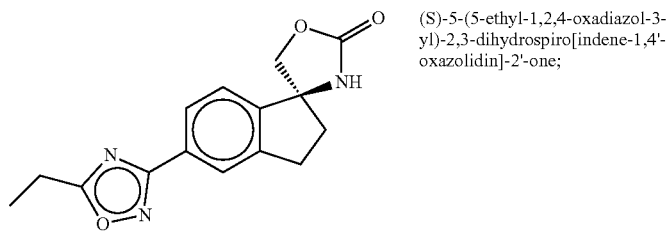

(S)-5-(5-ethyl-1,2,4-oxadiazol-3-yl)-2,3-dihydrospiro[indene-1,4'-oxazolidin]-2'-one;

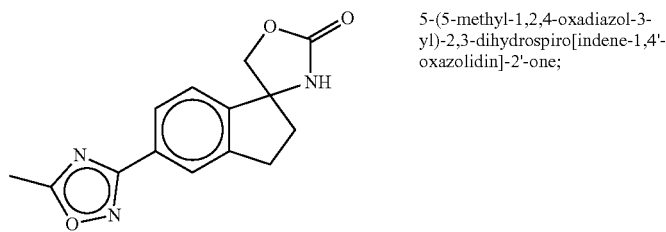

5-(5-methyl-1,2,4-oxadiazol-3-yl)-2,3-dihydrospiro[indene-1,4'-oxazolidin]-2'-one;

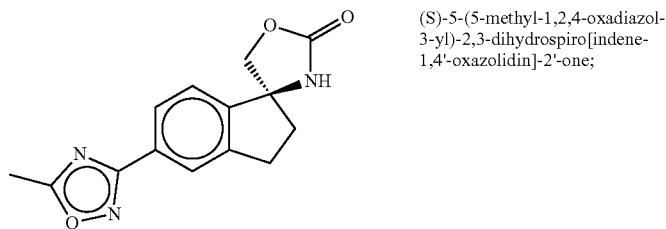

(S)-5-(5-methyl-1,2,4-oxadiazol-3-yl)-2,3-dihydrospiro[indene-1,4'-oxazolidin]-2'-one;

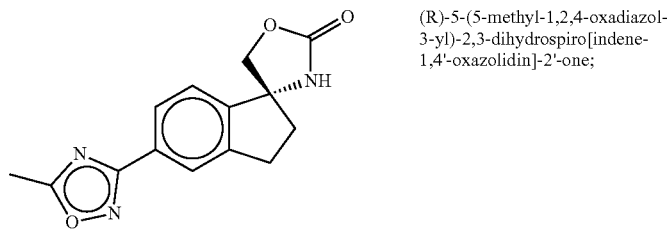

(R)-5-(5-methyl-1,2,4-oxadiazol-3-yl)-2,3-dihydrospiro[indene-1,4'-oxazolidin]-2'-one;

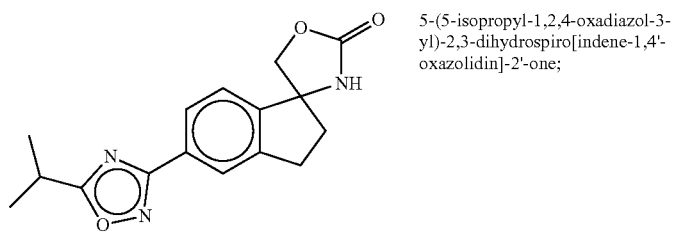
5-(5-isopropyl-1,2,4-oxadiazol-3-yl)-2,3-dihydrospiro[indene-1,4'-oxazolidin]-2'-one;

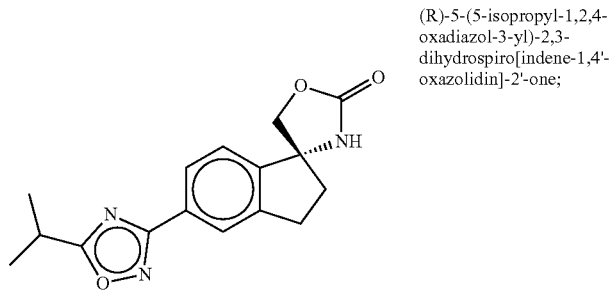
(R)-5-(5-isopropyl-1,2,4-oxadiazol-3-yl)-2,3-dihydrospiro[indene-1,4'-oxazolidin]-2'-one;

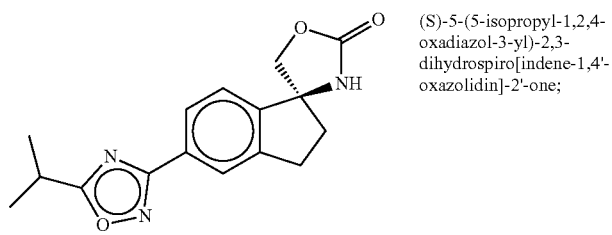
(S)-5-(5-isopropyl-1,2,4-oxadiazol-3-yl)-2,3-dihydrospiro[indene-1,4'-oxazolidin]-2'-one;

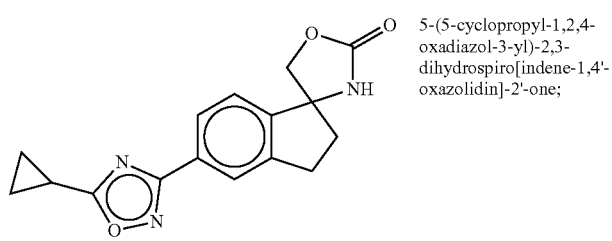
5-(5-cyclopropyl-1,2,4-oxadiazol-3-yl)-2,3-dihydrospiro[indene-1,4'-oxazolidin]-2'-one;

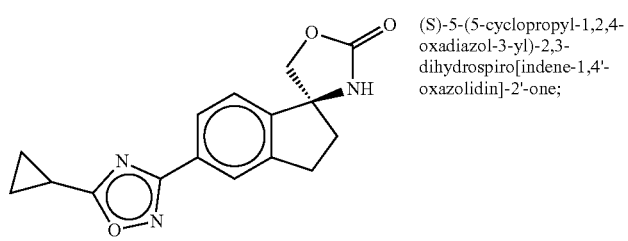
(S)-5-(5-cyclopropyl-1,2,4-oxadiazol-3-yl)-2,3-dihydrospiro[indene-1,4'-oxazolidin]-2'-one;

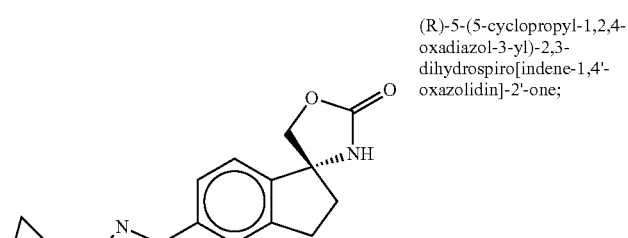
(R)-5-(5-cyclopropyl-1,2,4-oxadiazol-3-yl)-2,3-dihydrospiro[indene-1,4'-oxazolidin]-2'-one;

-continued

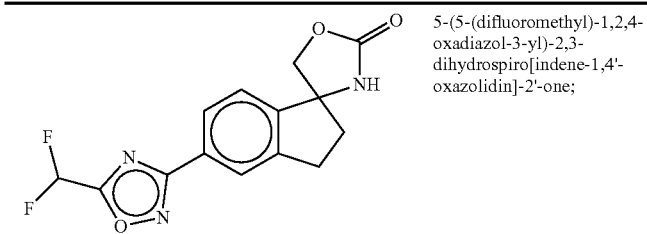
5-(5-(difluoromethyl)-1,2,4-oxadiazol-3-yl)-2,3-dihydrospiro[indene-1,4'-oxazolidin]-2'-one;

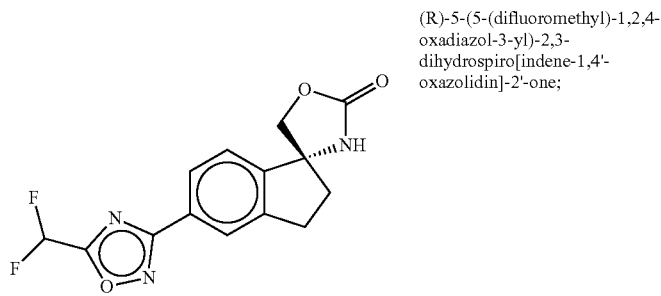
(R)-5-(5-(difluoromethyl)-1,2,4-oxadiazol-3-yl)-2,3-dihydrospiro[indene-1,4'-oxazolidin]-2'-one;

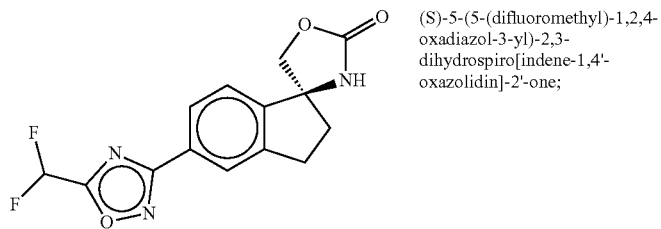
(S)-5-(5-(difluoromethyl)-1,2,4-oxadiazol-3-yl)-2,3-dihydrospiro[indene-1,4'-oxazolidin]-2'-one;

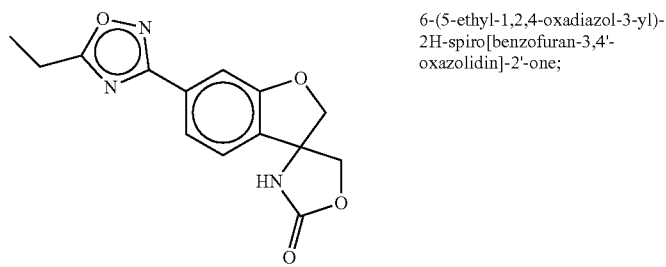
6-(5-ethyl-1,2,4-oxadiazol-3-yl)-2H-spiro[benzofuran-3,4'-oxazolidin]-2'-one;

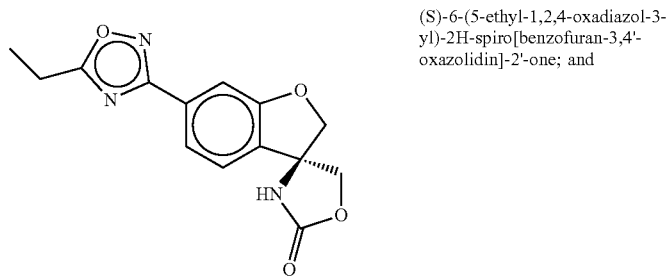
(S)-6-(5-ethyl-1,2,4-oxadiazol-3-yl)-2H-spiro[benzofuran-3,4'-oxazolidin]-2'-one; and

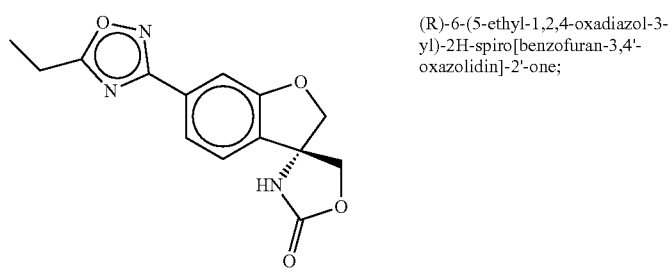
(R)-6-(5-ethyl-1,2,4-oxadiazol-3-yl)-2H-spiro[benzofuran-3,4'-oxazolidin]-2'-one;

or a pharmaceutically acceptable salt thereof.

10. A pharmaceutical composition comprising a compound of claim 1, or a pharmaceutically acceptable salt thereof, and a pharmaceutically acceptable excipient.

11. A method of treating heart disease in a subject in need thereof, comprising administering to the subject a compound of claim 1, or a pharmaceutically acceptable salt thereof.

12. The method of claim 11, wherein the heart disease is hypertrophic cardiomyopathy.

13. The method of claim 12, wherein the hypertrophic cardiomyopathy is obstructive or nonobstructive or is caused by sarcomeric and/or non-sarcomeric mutations.

14. The method of claim 11, wherein the heart disease is heart failure with preserved ejection fraction.

15. The method of claim 11, wherein the heart disease is selected from the group consisting of diastolic dysfunction, primary or secondary restrictive cardiomyopathy, myocardial infarction, angina pectoris, left ventricular outflow tract obstruction, hypertensive heart disease, congenital heart disease, cardiac ischemia, coronary heart disease, diabetic heart disease, congestive heart failure, right heart failure, cardiorenal syndrome, and infiltrative cardiomyopathy.

16. The method of claim 11, wherein the heart disease is or is related to one or more conditions selected from the group consisting of cardiac senescence, diastolic dysfunction due to aging, left ventricular hypertrophy and concentric left ventricular remodeling.

17. A method of treating a disease or condition that is associated with small left ventricular cavity, cavity obliteration, hyperdynamic left ventricular contraction, myocardial ischemia, or cardiac fibrosis in a subject in need thereof, comprising administering to the subject a compound of claim 1, or a pharmaceutically acceptable salt thereof.

18. A method of inhibiting a cardiac sarcomere, comprising contacting the cardiac sarcomere with a compound of claim 1, or a pharmaceutically acceptable salt thereof.

* * * * *